United States Patent
Smits et al.

(10) Patent No.: US 11,319,560 B2
(45) Date of Patent: *May 3, 2022

(54) PROCESS FOR ENZYMATIC HYDROLYSIS OF LIGNOCELLULOSIC MATERIAL AND FERMENTATION OF SUGARS

(71) Applicant: DSM IP ASSETS B.V., Heerlen (NL)

(72) Inventors: Johannes Petrus Smits, Echt (NL); Elisabeth Maria Gierveld, Echt (NL)

(73) Assignee: DSM IP ASSETS B.V., Heerlen (NL)

( * ) Notice: Subject to any disclaimer, the term of this patent is extended or adjusted under 35 U.S.C. 154(b) by 0 days.

This patent is subject to a terminal disclaimer.

(21) Appl. No.: 17/023,501

(22) Filed: Sep. 17, 2020

(65) Prior Publication Data

US 2021/0002676 A1 Jan. 7, 2021

Related U.S. Application Data

(63) Continuation of application No. 16/546,651, filed on Aug. 21, 2019, now Pat. No. 10,865,427, which is a continuation of application No. 15/519,819, filed as application No. PCT/EP2015/074091 on Oct. 19, 2015, now Pat. No. 10,435,718.

(30) Foreign Application Priority Data

Oct. 21, 2014 (EP) .................................... 14189619
Jun. 15, 2015 (EP) .................................... 15172060

(51) Int. Cl.
| | | |
|---|---|---|
| *C12P 7/10* | (2006.01) | |
| *C12P 19/02* | (2006.01) | |
| *C12P 19/14* | (2006.01) | |
| *C13K 13/00* | (2006.01) | |
| *C13K 1/02* | (2006.01) | |
| *C02F 3/28* | (2006.01) | |
| *C02F 3/34* | (2006.01) | |
| *C12P 7/14* | (2006.01) | |

(52) U.S. Cl.
CPC ................ *C12P 7/10* (2013.01); *C02F 3/28* (2013.01); *C02F 3/34* (2013.01); *C12P 7/14* (2013.01); *C12P 19/02* (2013.01); *C12P 19/14* (2013.01); *C13K 1/02* (2013.01); *C13K 13/00* (2013.01); *C13K 13/002* (2013.01); *C12P 2201/00* (2013.01); *C12P 2203/00* (2013.01); *Y02E 50/10* (2013.01)

(58) Field of Classification Search
None
See application file for complete search history.

(56) References Cited

U.S. PATENT DOCUMENTS

| | | |
|---|---|---|
| 10,144,939 B2 | 12/2018 | Noordam et al. |
| 10,337,040 B2 | 7/2019 | Noordam et al. |
| 10,597,689 B2 | 3/2020 | Noordam et al. |
| 2009/0098616 A1 | 4/2009 | Burke et al. |
| 2020/0048669 A1 | 2/2020 | Noordam et al. |

FOREIGN PATENT DOCUMENTS

| | | |
|---|---|---|
| CN | 101855358 A | 10/2010 |
| CN | 106255760 A | 12/2016 |
| WO | 2009/046538 A1 | 4/2009 |
| WO | 2010/080407 A2 | 7/2010 |
| WO | 2011/157427 A1 | 12/2011 |
| WO | 2013/088001 A2 | 6/2013 |
| WO | 2014/039984 A1 | 3/2014 |
| WO | 2014/072392 A1 | 5/2014 |
| WO | 2014/075694 A1 | 5/2014 |
| WO | 2014/108454 A1 | 7/2014 |
| WO | 2015/165952 A1 | 11/2015 |

OTHER PUBLICATIONS

Anonymous: "Accelerase Duet, product information sheet", Jan. 1, 2010, pp. 1-4, www.genencor.com/fileadmin/user_upload/genencor/documents/accellerase_duet_product_info_sheet.pdf.
International Search Report of International Patent Application No. PCT/EP2015/074091 dated Dec. 22, 2015.

*Primary Examiner* — Suzanne M Noakes
(74) *Attorney, Agent, or Firm* — McBee Moore & Vanik IP, LLC; Susan McBee; Chester Moore

(57) ABSTRACT

The invention relates to a process for the preparation of a sugar and/or fermentation product from lignocellulosic material.

15 Claims, No Drawings

PROCESS FOR ENZYMATIC HYDROLYSIS OF LIGNOCELLULOSIC MATERIAL AND FERMENTATION OF SUGARS

CROSS-REFERENCE TO RELATED APPLICATIONS

This application is a continuation of U.S. patent application Ser. No. 16/546,651, filed Aug. 21, 2019, which is a continuation of U.S. patent application Ser. No. 15/519,819, filed 17 Apr. 2017, now U.S. Pat. No. 10,435,718, issued Oct. 8, 2019, which is a National Stage entry of International Application No. PCT/EP2015/074091, filed Oct. 19, 2015, which claims priority to European Patent Application No. 15172060.4, filed Jun. 15, 2015 and European Patent Application No. 14189619.1, filed Oct. 21, 2014. Each of these applications is incorporated by reference in its entirety.

FIELD OF THE INVENTION

The invention relates to a process for the enzymatic hydrolysis of lignocellulosic material and fermentation of sugars.

BACKGROUND OF THE INVENTION

Lignocellulosic material is primarily composed of cellulose, hemicellulose and lignin and provides an attractive platform for generating alternative energy sources to fossil fuels. The material is available in large amounts and can be converted into valuable products e.g. sugars or biofuel, such as bioethanol.

Producing fermentation products from lignocellulosic material is known in the art and generally includes the steps of pretreatment, hydrolysis, fermentation, and optionally recovery of the fermentation products.

During the hydrolysis, which may comprise the steps of liquefaction, pre-saccharification and/or saccharification, cellulose present in the lignocellulosic material is partly (typically 30 to 95%, dependable on enzyme activity and hydrolysis conditions) converted into reducing sugars by cellulolytic enzymes. The hydrolysis typically takes place during a process lasting 6 to 168 hours (see Kumar, S., Chem. Eng. Technol. 32 (2009), 517-526) under elevated temperatures of 45 to 50° C. and non-sterile conditions.

Commonly, the sugars are then converted into valuable fermentation products such as ethanol by microorganisms like yeast. The fermentation takes place in a separate, preferably anaerobic, process step, either in the same or in a different vessel. The temperature during fermentation is adjusted to 30 to 33° C. to accommodate growth and ethanol production by microorganisms, commonly yeasts. During the fermentation process, the remaining cellulosic material is converted into reducing sugars by the enzymes already present from the hydrolysis step, while microbial biomass and ethanol are produced. The fermentation is finished once the cellulosic material is converted into fermentable sugars and all fermentable sugars are converted into ethanol, carbon dioxide and microbial biomass. This may take up to 6 days. In general, the overall process time of hydrolysis and fermentation may amount up to 13 days.

In general, cost of enzyme production is a major cost factor in the overall production process of fermentation products from lignocellulosic material (see Kumar, S., Chem. Eng. Technol. 32 (2009), 517-526). Thus far, reduction of enzyme production costs is achieved by applying enzyme products from a single or from multiple microbial sources (see WO 2008/008793) with broader and/or higher (specific) hydrolytic activity. This leads to a lower enzyme need, faster conversion rates and/or a higher conversion yields, and thus to lower overall production costs.

Next to the optimization of enzymes, optimization of process design is a crucial tool to reduce overall costs of the production of fermentation products.

For economic reasons, it is therefore desirable to include new and innovative process configurations aimed at reducing overall production costs in the process involving hydrolysis and fermentation of lignocellulosic material.

SUMMARY OF THE INVENTION

An object of the invention is to provide an improved process for the preparation of a sugar product and/or a fermentation product from lignocellulosic material. Another object is to provide a process involving hydrolysis, wherein the process conditions of the hydrolysis are optimized. Optimization lies in any of the following features.

The hydrolysis process performed in the present invention comprises at least two steps, a feeding step and a saccharification step. Said steps can be performed in different containers. The feeding step starts by adding lignocellulosic material to a container wherein an enzyme composition is present. So, enzymes used in the hydrolysis process are present at the start of the feeding step. During the feeding step the lignocellulosic material is liquefied by the enzymes and sugars are released. The rate of addition of the lignocellulosic material to the container is determined by the viscosity of the material present in the container. So, the viscosity of the material in the container can be controlled. Preferably, the lignocellulosic material in the container is kept liquid during the feeding step and is thus easily miscible. This reduces energy costs, decreases mixing intensity and therefore leads to an overall more efficient production process.

In addition, this hydrolysis process has the advantage that the pH can be adjusted online in the container wherein the feeding step and/or the saccharification step take place and that there is no need to adjust the pH of the lignocellulosic material prior to addition to the container.

During the saccharification step the viscosity of the lignocellulosic material does not change substantially compared to the viscosity of the material present in the container during the feeding step.

During the feeding step and/or saccharification step oxygen can be supplied to the containers, for instance to the headspace of the containers. By the addition of oxygen it is possible to attain many process advantages, including optimal temperature conditions, reduced process time, reduced dosage of enzyme, re-use of enzymes, higher yields and other process optimizations, resulting in reduced costs.

As the addition rate of the lignocellulosic material can be controlled, the supply of lignocellulosic material can be balanced with the oxygen need per type of lignocellulosic material.

Moreover, by allowing the lignocellulosic material to pass the oxygen-rich headspace of a container, oxygen can directly be supplied to the lignocellulosic material. So, there may be no need for additional aeration by means of for instance bubbles or through rigorous stirring. This avoids foaming and reduces the energy consumption required for stirring and/or creating a gas flow through the material in the container.

Furthermore, by using different enzymes during the feeding step and the saccharification step, the hydrolysis process can be further optimized. For example, an enzyme composition comprising at least two cellulases such as endoglucanases and/or lytic polysaccharide monooxygenases can be used during the feeding step, while an enzyme composition comprising at least two cellulases such as cellobiohydrolases and beta-glucosidases can be used during the saccharification phase.

During the feeding step, heat is easily transferred into the material present in the container, as the low viscosity allows homogeneous mixing and thus equal dividing of heat and temperature. This makes it possible to optimize and minimize power input for heating and avoids local temperature build up that might inactivate enzyme activity.

Due to the controlled low viscosity level during the feeding step and saccharification step, dissolved oxygen level can be controlled without extensive stirring or mixing. This makes it possible to optimize and minimize power input for oxygen supply and avoids local differences in dissolved oxygen concentration that might result in local variation of enzyme activity. Due to the control of dissolved oxygen, enzyme inactivation due to oxidation can be limited.

By using the processes of the present invention, it is possible to attain many process advantages, including optimal temperature conditions, reduced process time, reduced dosage of enzyme, re-use of enzymes and other process optimizations, resulting in reduced costs. Advantageously, the invention provides processes in which the hydrolysis step is conducted at improved conditions. The invention also provides a process involving hydrolysis having a reduced process time. The invention furthermore provides a process that is simple and robust.

DETAILED DESCRIPTION OF THE INVENTION

Throughout the present specification and the accompanying claims, the words "comprise" and "include" and variations such as "comprises", "comprising", "includes" and "including" are to be interpreted inclusively. That is, these words are intended to convey the possible inclusion of other elements or integers not specifically recited, where the context allows. The articles "a" and "an" are used herein to refer to one or to more than one (i.e. to one or at least one) of the grammatical object of the article. By way of example, "an element" may mean one element or more than one element.

The present invention relates to a process for the preparation of a sugar product from lignocellulosic material, comprising the following steps: (a) optionally, pretreatment of the lignocellulosic material; (b) optionally, washing of the optionally pretreated lignocellulosic material; (c) fed-batch addition of the optionally washed and/or optionally pretreated lignocellulosic material to a first container that comprises an enzyme composition comprising at least two cellulases; (d) enzymatic hydrolysis of the optionally washed and/or optionally pretreated lignocellulosic material in the first container using the enzyme composition comprising at least two cellulases to liquefy the lignocellulosic material; (e) addition of the liquefied lignocellulosic material to a second container; (f) enzymatic hydrolysis of the liquefied lignocellulosic material in the second container using an enzyme composition comprising at least two cellulases to obtain a sugar product; and (g) optionally, recovery of the sugar product.

The current invention also covers a process wherein step (e) is optional, i.e. a process for the preparation of a sugar product from lignocellulosic material, comprising the following steps: (a) optionally, pretreatment of the lignocellulosic material; (b) optionally, washing of the optionally pretreated lignocellulosic material; (c) fed-batch addition of the optionally washed and/or optionally pretreated lignocellulosic material to a first container that comprises an enzyme composition comprising at least two cellulases; (d) enzymatic hydrolysis of the optionally washed and/or optionally pretreated lignocellulosic material in the first container using the enzyme composition comprising at least two cellulases to liquefy the lignocellulosic material; (e) optionally, addition of the liquefied lignocellulosic material to a second container; (f) enzymatic hydrolysis of the liquefied lignocellulosic material in the first and/or second container using an enzyme composition comprising at least two cellulases to obtain a sugar product; and (g) optionally, recovery of the sugar product.

The present invention also relates to a process for the preparation of a fermentation product from lignocellulosic material, comprising the following steps: (a) optionally, pretreatment of the lignocellulosic material; (b) optionally, washing of the optionally pretreated lignocellulosic material; (c) fed-batch addition of the optionally washed and/or optionally pretreated lignocellulosic material to a first container that comprises an enzyme composition comprising at least two cellulases; (d) enzymatic hydrolysis of the optionally washed and/or optionally pretreated lignocellulosic material in the first container using the enzyme composition comprising at least two cellulases to liquefy the lignocellulosic material; (e) addition of the liquefied lignocellulosic material to a second container; (f) enzymatic hydrolysis of the liquefied lignocellulosic material in the second container using an enzyme composition comprising at least two cellulases to obtain a hydrolysed lignocellulosic material; (g) optionally, recovery of the hydrolysed lignocellulosic material; (h) fermentation of the hydrolysed lignocellulosic material to produce a fermentation product; and (i) optionally, recovery of the fermentation product.

The current invention also covers a process wherein step (e) is optional, i.e. a process for the preparation of a fermentation product from lignocellulosic material, comprising the following steps: (a) optionally, pretreatment of the lignocellulosic material; (b) optionally, washing of the optionally pretreated lignocellulosic material; (c) fed-batch addition of the optionally washed and/or optionally pretreated lignocellulosic material to a first container that comprises an enzyme composition comprising at least two cellulases; (d) enzymatic hydrolysis of the optionally washed and/or optionally pretreated lignocellulosic material in the first container using the enzyme composition comprising at least two cellulases to liquefy the lignocellulosic material; (e) optionally, addition of the liquefied lignocellulosic material to a second container; (f) enzymatic hydrolysis of the liquefied lignocellulosic material in the first and/or second container using an enzyme composition comprising at least two cellulases to obtain a hydrolysed lignocellulosic material; (g) optionally, recovery of the hydrolysed lignocellulosic material; (h) fermentation of the hydrolysed lignocellulosic material to produce a fermentation product; and (i) optionally, recovery of the fermentation product.

Step (d) of the processes according to the present invention can also be called feeding step, while step (f) of the processes according to the present invention can also be called saccharification step. In the feeding step the optionally washed and/or optionally pretreated lignocellulosic material is added in a fed-batch mode to the container comprising the enzyme composition.

The term "first container" as used herein can mean a single container, but can also mean a group of containers. The term "second container" as used herein can mean a single container, but can also mean a group of containers.

In step (c) of the processes according to the present invention lignocellulosic material that is optionally washed and/or optionally pretreated is added to a first container wherein an enzyme composition comprising at least two cellulases is already present. The enzyme composition present in the first container may be an aqueous composition. In an embodiment the enzyme composition present in the first container comprises an amount of lignocellulosic material before the lignocellulosic material that is optionally washed and/or optionally pretreated is added to a first container. In an embodiment the dry matter content of the enzyme composition that already comprises some lignocellulosic material is from 0.01-5% wt %. The lignocellulosic material that may be already present in the enzyme composition may optionally be washed and/or optionally be pretreated. The lignocellulosic material that may be already present in the enzyme composition may optionally be liquefied. The presence of some lignocellulosic material in the enzyme composition before lignocellulosic material is added to the first container may lead to an increased stability of the enzymes present in the first container. In a preferred embodiment in step (c) of the processes according to the present invention lignocellulosic material that is optionally washed and/or optionally pretreated is added in a fed-batch mode to a first container wherein an enzyme composition comprising at least two cellulases is already present. In an embodiment optionally washed and/or optionally pretreated lignocellulosic material is added during step (d) of the processes according to the present invention. This means that the optionally washed and/or optionally pretreated lignocellulosic material is added in portions to the container wherein an enzyme composition comprising at least two cellulases is already present. Ergo, in step (c) of the processes according to the present invention lignocellulosic material that is optionally washed and/or optionally pretreated is added in a fed-batch mode to a first container wherein an enzyme composition comprising at least two cellulases is already present.

In an embodiment additional enzymes are added during step (d) and/or step (f) of the processes according to the present invention.

In an embodiment the viscosity of the lignocellulosic material in the first container during step (d) of the processes according to the present invention is controlled by adjusting the addition rate of the optionally washed and/or optionally pretreated lignocellulosic material. The viscosity of the lignocellulosic material in the first container during step (d) of the processes according to the present invention is kept below 1000 cP. In an embodiment the viscosity of the lignocellulosic material in the first container during step (d) of the processes according to the present invention is kept between 10 and 1000 cP, between 10 and 900 cP, between 10 and 800 cP, between 10 and 700 cP, between 10 and 600 cP, between 10 and 500 cP, between 10 and 400 cP, between 10 and 300 cP, between 10 and 200 cP and preferably between 10 and 100 cP. The viscosity can be determined with a Brookfield DV III Rheometer at the temperature used for the hydrolysis.

In an embodiment an aqueous composition, optionally an aqueous enzyme composition comprising at least two cellulases, is added to the first container.

In an embodiment oxygen is added to the first container and/or second container. In an embodiment oxygen is added to the first container and/or second container during a single part or multiple parts of the process time.

Oxygen can be added in several ways. For example oxygen can be added as oxygen gas, oxygen-enriched gas, such as oxygen-enriched air, or air. Oxygen may also be added by means of in situ oxygen generation. For example, oxygen may be generated by electrolysis, oxygen may be produced enzymatically, e.g. by the addition of peroxide, or oxygen may be produced chemically, e.g. by an oxygen generating system such as $KHSO_5$. For example, oxygen is produced from peroxide by catalase. The peroxide can be added in the form of dissolved peroxide or generated by an enzymatic or chemical reaction. In case catalase is used as enzyme to produce oxygen, catalase present in the enzyme composition for the hydrolysis can be used or catalase can be added for this purpose.

Oxygen can be added continuously or discontinuously. Examples how to add oxygen include, but are not limited to, addition of oxygen to the liquid phase comprising the lignocellulosic material in the container (for instance as bubbles) and addition of oxygen to the headspace of the container. When oxygen is added to the headspace of the container and the lignocellulosic material is passed through the oxygen-rich headspace, sufficient oxygen necessary for the hydrolysis reaction may be supplied. In general, the amount of oxygen added to the first and/or second container can be controlled and/or varied. Restriction of the oxygen supplied is possible by adding only oxygen during part of the hydrolysis time in said container. Another option is adding oxygen at a low concentration, for example by using an mixture of air and recycled air (air leaving the container) or by "diluting" air with an inert gas. Increasing the amount of oxygen added can be achieved by addition of oxygen during longer periods of the hydrolysis time, by adding the oxygen at a higher concentration or by adding more air. Another option for changing the oxygen uptake is varying the hydrolysis temperature. A higher hydrolysis temperature will cause a lower maximal saturation concentration of the oxygen in the container content. Another way to control the oxygen concentration is to add an oxygen consumer and/or an oxygen generator. The addition of the oxygen to the cellulolytic material can be done before and/or during the enzymatic hydrolysis. Oxygen can be introduced, for example blown, into the liquid hydrolysis container contents of lignocellulosic material. It can also be blown into the headspace of the container.

In an embodiment oxygen is added to the first and/or second container before and/or during the addition of the lignocellulosic material to said container. The oxygen may be introduced together with the lignocellulosic material that enters the hydrolysis container. In an embodiment oxygen is added to the lignocellulosic material before and/or during addition of the lignocellulosic material to the first container. The oxygen may be introduced into the material stream that will enter the container or with part of the container contents that passes an external loop of the container.

Oxygen may be added before hydrolysis, during a part of hydrolysis, during whole hydrolysis or any combination thereof. In case the oxygen present in the hydrolysis container contents or the sugar product or the hydrolysate formed in the hydrolysis step might influence or disturb in the subsequent fermentation step, oxygen may be added, except for the last part of the hydrolysis in step (f). This way (most of) the oxygen may be consumed before the hydrolyzed lignocellulosic material is fermented.

In an embodiment, the oxygen concentration (DO) in the lignocellulosic material present during the enzymatic hydrolysis in step (f) of the processes of the present invention, is at least 0.001 mol/m$^3$, preferably at least 0.002 mol/m$^3$, more preferably at least 0.003 mol/m$^3$, even more preferably at least 0.01 mol/m$^3$, most preferably at least 0.02 mol/m$^3$ and in particular at least 0.03 mol/m$^3$. In reactors of less than 1 m$^3$ an oxygen concentration in the lignocellulosic material of below 0.01 mol/m$^3$ or 0.02 mol/m$^3$ will be obtained by slow stirring. Vigorous mixing or stirring at such scale introduces part of the gas phase of the headspace into the reaction liquid. For example, the mixing or stirring may create a whirlpool that draws oxygen into the liquid. In general flushing the headspace with air in combination with (vigorous) mixing or stirring will introduce sufficient oxygen into the cellulosic material in the hydrolysis container for containers up to a size of 100 liter to 1 m$^3$. At larger scale, for example in a reactor of 50 m$^3$ or more, for example 100 m$^3$, so much energy is needed for vigorous stirring that from economic point of view this will not be applied in a commercially operating process.

In an embodiment the oxygen concentration (DO) in the lignocellulosic material present during the enzymatic hydrolysis in step (d) and/or step (f) of the processes of the present invention is preferably at most 80% of the saturation concentration of oxygen under the hydrolysis reaction conditions, more preferably at most 0.12 mol/m$^3$, still more preferably at most 0.09 mol/m$^3$, even more preferably at most 0.06 mol/m$^3$, most preferably at most 0.045 mol/m$^3$ and in particular at most 0.03 mol/m$^3$. Temperature and pressure will influence the DO.

The preferred and exemplary mol/m$^3$ values given above relate to normal atmospheric pressure and a temperature of about 62° C. The skilled person in the art will appreciate favourable DO values on basis of the present teachings.

In the enzymatic hydrolysis amorphous and crystalline polysaccharides or cellulose are hydrolysed to sugars such as glucose. Amorphous polysaccharides are for example converted to oligosaccharides by endoglucanases and then the oligosaccharides can be converted by cellobiohydrolases and beta-glucosidases to glucose. The conversion of the crystalline polysaccharides may occur in parallel or sequential and continue even when most of the amorphous polysaccharides are hydrolysed. The addition of oxygen in combination with lytic polysaccharide monooxygenases is beneficial during the hydrolysis of the crystalline polysaccharides for example in the degradation of the polysaccharides into oligosaccharides. The crystalline glucan structure can be opened by lytic polysaccharide monooxygenases. This type of enzyme opens up the structure by oxidizing the glycosidic bonds and making it accessible for the other cellulolytic enzymes for further hydrolysing the oligosaccharides into glucose. The addition of oxygen is very useful, especially in the phase wherein crystalline polysaccharides are converted by enzymes. Outside this phase, no addition of oxygen or adding less oxygen may be more efficient.

The processes of the present invention show advantages, especially on pilot plant and industrial scale. In an embodiment the first container and/or second container has a volume of at least 1 m$^3$. Preferably, the first container and/or second container has a volume of at least 1 m$^3$, at least 2 m$^3$, at least 3 m$^3$, at least 4 m$^3$, at least 5 m$^3$, at least 6 m$^3$, at least 7 m$^3$, at least 8 m$^3$, at least 9 m$^3$, at least 10 m$^3$, at least 15 m$^3$, at least 20 m$^3$, at least 25 m$^3$, at least 30 m$^3$, at least 35 m$^3$, at least 40 m$^3$, at least 45 m$^3$, at least 50 m$^3$, at least 60 m$^3$, at least 70 m$^3$, at least 75 m$^3$, at least 80 m$^3$, at least 90 m$^3$, at least 100 m$^3$, at least 200 m$^3$, at least 300 m$^3$, at least 400 m$^3$, at least 500 m$^3$, at least 600 m$^3$, at least 700 m$^3$, at least 800 m$^3$, at least 900 m$^3$, at least 1000 m$^3$, at least 1500 m$^3$, at least 2000 m$^3$, at least 2500 m$^3$. In general, the container will be smaller than 3000 m$^3$ or 5000 m$^3$. The first container and the second container may have the same volume, but also may have a different volume. In case, several first containers and/or second containers are used, they may have the same volume, but also may have a different volume.

The process of the invention is advantageously applied in combination with the use of thermostable enzymes. In an embodiment the enzyme composition is derived from a fungus, preferably a microorganism of the genus *Rasamsonia*, or the enzyme composition comprises a fungal enzyme, preferably a *Rasamsonia* enzyme. Cellulolytic enzymes of *Rasamsonia* applied on pretreated lignocellulosic feedstock show maximal conversion rates at temperature within the range of 50 to 70° C. The enzymes remain active under these circumstances for 14 days and more without complete cessation of activity. By using optimal temperature conditions, a maximal amount of reducing sugars can be released from lignocellulosic material (total hydrolysis) within the shortest possible hydrolysis time. In this way, 100% conversion of cellulose in glucose can be achieved in less than 5 days. The theoretical maximum yield (Yps max in g product per gram glucose) of a fermentation product can be derived from textbook biochemistry. For ethanol, 1 mole of glucose (180 g) yields according to normal glycolysis fermentation pathway in yeast 2 moles of ethanol (=2×46=92 g ethanol). The theoretical maximum yield of ethanol on glucose is therefore 92/180=0.511 g ethanol/g glucose. For butanol (MW 74 g/mole) or isobutanol, the theoretical maximum yield is 1 mole of butanol per mole of glucose. So Yps max for (iso-)butanol=74/180=0.411 g (iso-)butanol/g glucose. For lactic acid the fermentation yield for homolactic fermentation is 2 moles of lactic acid (MW=90 g/mole) per mole of glucose. According to this stoichiometry, the Yps max=1 g lactic acid/g glucose. For other fermentation products a similar calculation may be made. The cost reduction achieved with applying cellulolytic enzymes of *Rasamsonia* are the result of an overall process time reduction.

Due to the high stability of the enzymes used in the processes of the present invention, it is possible to lower the enzyme dosage and extend the use of the enzyme by prolonging the hydrolysis times. For example, 0.175 mL enzyme/g lignocellulosic material dry matter results in release of approximately 90% of the theoretical maximum of reducing sugars from pretreated lignocellulosic material within 72 h. When using 0.075 mL enzyme/g lignocellulosic material dry matter, approximately 90% conversion of the theoretical maximum is achieved within 120 h. The results show that, because of the stability of the enzyme activity, lowering the enzyme dosage can be compensated by extending the hydrolysis time to obtain the same amount of reducing sugars. The cost reduction achieved by using stable cellulolytic enzymes, such as those of *Rasamsonia*, results in lower enzyme dosages that nevertheless result in similar hydrolysis conversion yields.

In a common process for converting lignocellulosic material into ethanol, process steps are preferably done under septic conditions to lower the operational costs. Contamination and growth of contaminating microorganisms can therefore occur and result in undesirable side effects, such as lactic acid, formic acid and acetic acid production, yield losses of ethanol on substrate, production of toxins and extracellular polysaccharides. These effects may affect production costs significantly. A high process temperature and/ or a short process time limits the risk on contamination during hydrolysis and fermentation. Thermostable enzymes, like those of *Rasamsonia*, are capable of hydrolysing lignocellulosic material at temperatures of higher than 60° C. At these temperatures, the risk that a contaminating microorganism will cause undesired side effects is little to almost zero.

During the fermentation step, in which ethanol is produced, temperatures are typically between 30 to 37° C. and are preferably not raised because of production losses. By applying short fermentation process times, the risks and effects of contamination and/or growth of contaminants are reduced as much as possible. With stable enzymes, like those of *Rasamsonia*, a short fermentation time can be applied and thus risks of contamination and/or growth of contaminants are reduced as much as possible. The cost reduction achieved with applying thermostable cellulolytic enzymes of *Rasamsonia* in this way, results in a lower risk of process failures due to contamination.

The first step after thermal pretreatment is to cool the pretreated material to temperatures wherein the enzymes have an optimal activity. On large scale, this is typically done by adding (cooled) water, which, besides decreasing the temperature, reduces the dry matter content. By using thermostable enzymes, like those of *Rasamsonia*, cost reduction can be achieved, because (i) less cooling of the pretreated material is required since higher temperatures are allowed during hydrolysis, and (ii) less water is added, which increases the dry matter content during hydrolysis and fermentation and thus increase the ethanol production capacity (amount produced per time unit per volume) of an ethanol plant. By using thermostable enzymes, like those of *Rasamsonia*, cost reduction may also be achieved by using cooling water having a higher temperature than the water that is used in a process with non-thermostable enzyme.

At the end of the hydrolysis, enzyme activities appear to be low, since little reducing sugars are released once almost all cellulose is converted. The amount of enzymatic activity present, however, has decreased only a little, assumingly mainly due to absorption of the enzymes to the substrate. By applying solid-liquid separation after hydrolysis, such as centrifugation, filtration, cantation, sedimentation, 60% or more (e.g. 70%) of the enzyme activity in solution can be recovered and re-used for hydrolysis of a new pretreated lignocellulosic material during the next hydrolysis.

Moreover, after solid-liquid separation the enzyme in solution can be separated from the solution containing reducing sugars and other hydrolysis products from the enzymatic actions. This separation can be done by techniques including, but not limited to, ultra- and microfiltration, centrifugation, cantation, sedimentation, with or without first adsorption of the enzyme to a carrier of any kind. For example, after hydrolysis of pretreated material with 0.175 mL/g material dry matter enzyme load for 20 h, 50% of the theoretical maximum amount of reducing sugars is liberated and after the same hydrolysis for 72 h, 90% of the theoretical maximum amount of reducing sugars is liberated. By centrifugation and ultrafiltration, 60-70% of the enzyme activity was recovered in the retentate, while the filtrate contained more than 80% of the liberated reducing sugars. By re-using the retentate, either as it is or after further purification and/or concentration, enzyme dosage during the next hydrolysis step can be reduced with 60 to 70%. The cost reduction achieved by using stable cellulolytic enzymes, such as those of *Rasamsonia*, in this way is the consequence of a lower enzyme dosage.

The process including enzyme recycling after hydrolysis, as described above, can be combined with recycling of the ethanol producing microorganism after fermentation and with the use of the reducing sugars containing filtrate as a substrate (purified and/or concentrated or diluted) in enzyme production fermentation and as substrate for the cultivation of the ethanol producing microorganism.

The thermostability of enzymes, like those from *Rasamsonia*, causes remaining cellulolytic activity after hydrolysis, fermentation and vacuum distillation in the thin stillage. The total activity of the enzyme is reduced during the three successive process steps. The thin stillage obtained after vacuum distillation can thus be re-used as a source of enzyme for a newly started hydrolysis-fermentation-distillation process cycle of pretreated material conversion into ethanol. The thin stillage can be used either in concentrated or (un)diluted form and/or purified and with or without additional enzyme supplementation.

In an optimal process, an amount of enzyme is supplemented into the thin stillage, before its re-use in a new process cycle, equal to the amount of activity lost during the three successive process steps of the previous process cycle. In this way over dosage of enzyme is avoided and thus most efficient use of enzyme is obtained. Moreover, by providing high enzyme dosage in the first process cycle, and supplementing enzyme equal to the amount of activity lost during the three successive process steps in the following process cycles, highest possible hydrolysis rates can be obtained in each process cycle resulting in short hydrolysis times of less than 48 h in combination with most efficient use of enzymes.

By applying mixing during hydrolysis, enzymes come more often in contact with substrates, which results in a more efficient use of the catalytic activity. This will result in a lower enzyme dosages and thus in lower costs, unless the mixing has a negative effect on the enzymes. Stable enzymes, like the thermostable enzymes from *Rasamsonia*, are robust and can resist circumstances of (locally) high shear and temperatures, which is the case during intensive mixing of slurries. The use of them in mixed systems is therefore beneficial and will lead to dosage and thus costs reduction.

A "thermostable" enzyme as used herein means that the enzyme has a temperature optimum of 60° C. or higher, 70° C. or higher, 75° C. or higher, 80° C. or higher, 85° C. or higher. They may for example be isolated from thermophilic microorganisms or may be designed by the skilled person and artificially synthesized. In one embodiment the polynucleotides may be isolated or obtained from thermophilic or thermotolerant filamentous fungi or isolated from non-thermophilic or non-thermotolerant fungi but are found to be thermostable.

By "thermophilic fungus" is meant a fungus that grows at a temperature of 50° C. or higher. By "themotolerant" fungus is meant a fungus that grows at a temperature of 45° C. or higher, having a maximum near 50° C.

Examples of thermophilic fungal strains are *Rasamsonia emersonii* (formerly known as *Talaromyces emersom*). *Talaromyces emersonii, Penicillium geosmithia emersonii* and *Rasamsonia emersonii* are used interchangeably herein.

Suitable thermophilic or thermotolerant fungal cells may be a *Humicola, Rhizomucor, Myceliophthora, Rasamsonia, Talaromyces, Thermomyces, Thermoascus* or *Thielavia* cell, preferably a *Rasamsonia* cell. Preferred thermophilic or thermotolerant fungi are *Humicola grisea* var. thermoidea, *Humicola lanuginosa, Myceliophthora thermophila, Papulaspora thermophilia, Rasamsonia byssochlamydoides, Rasamsonia emersonii, Rasamsonia argillacea, Rasamsonia*

*eburnean, Rasamsonia brevistipitata, Rasamsonia cylindrospora, Rhizomucor pusillus, Rhizomucor miehei, Talaromyces baciffisporus, Talaromyces leycettanus, Talaromyces thermophilus, Thermomyces lenuginosus, Thermoascus crustaceus, Thermoascus thermophilus Thermoascus aurantiacus* and *Thielavia terrestris*.

Thermophilic fungi are not restricted to a specific taxonomic order and occur all over the fungal tree of life. Examples are *Rhizomucor* in the Mucorales, *Myceliophthora* in Sordariales and *Talaromyces, Thermomyces* and *Thermoascus* in the Eurotiales (see Mouchacca, 1997). The majority of *Talaromyces* species are mesophiles, but exceptions are species within sections *Emersonii* and *Thermophila*. Section *Emersonii* includes *Talaromyces emersonii, Talaromyces byssochlamydoides, Talaromyces baciffisporus* and *Talaromyces leycettanus*, all of which grow well at 40° C. *Talaromyces baciffisporus* is thermotolerant, *Talaromyces leycettanus* is thermotolerant to thermophilic, and *Talaromyces emersonii* and *Talaromyces byssochlamydoides* are truly thermophilic (see Stolk and Samson, 1972). The sole member of *Talaromyces* section *Thermophila, Talaromyces thermophilus*, grows rapidly at 50° C. (see Stolk and Samson, 1972). The current classification of these thermophilic *Talaromyces* species is mainly based on phenotypic and physiological characters, such as their ability to grow above 40° C., ascospore color, the structure of ascornatal covering and the formation of a certain type of anamorph. Stolk and Samson (1972) stated that the members of the section *Emersonii* have anamorphs of either *Paecilomyces* (*Talaromyces byssochlamydoides* and *Talaromyces leycettanus*) or *Penicillium cylindrosporum* series (*Talaromyces emersonii* and *Talaromyces baciffisporus*). Later, Pitt (1979) transferred the species belonging to the *Penicillium cylindrosporum* series to the genus *Geosmithia*, based on various characters such as the formation of conidia from terminal pores instead of on collula (necks), a character of *Penicillium* and *Paecilomyces*. Within the genus *Geosmithia*, only *Geosmithia argillacea* is thermotolerant, and Stolk et al. (1969) and Evans (1971) proposed a connection with members of *Talaromyces* sect. *Emersonii*. The phylogenetic relationship of the themophilic *Talaromyces* species within *Talaromyces* and the Trichocomaceae is unknown. (see J. Houbraken, Antonie van Leeuwenhoek 2012 February; 101 (2): 403-21).

*Rasamsonia* is a new genus comprising thermotolerant and thermophilic *Talaromyces* and *Geosmithia* species (J. Houbraken et al., vida supra). Based on phenotypic, physiological and molecular data, Houbraken et al. proposed to transfer the species *Talaromyces emersonii, Talaromyces byssochlamydoides, Talaromyces eburneus, Geosmithia argillacea* and *Geosmithia cylindrospora* to *Rasamsonia* gen. nov.

Preferred thermophilic fungi are *Rasamsonia byssochlamydoides, Rasamsonia emersonii, Thermomyces lenuginosus, Talaromyces thermophilus, Thermoascus crustaceus, Thermoascus thermophilus* and *Thermoascus aurantiacus*, with *Rasamsonia emersonii* being most preferred.

"Filamentous fungi" include all filamentous forms of the subdivision Eumycota and Oomycota (as defined by Hawksworth et al., In, Ainsworth and Bisby's Dictionary of The Fungi, 8th edition, 1995, CAB International, University Press, Cambridge, UK). The filamentous fungi are characterized by a mycelial wall composed of chitin, cellulose, glucan, chitosan, mannan, and other complex polysaccharides. Vegetative growth is by hyphal elongation and carbon catabolism is obligatory aerobic. Filamentous fungal strains include, but are not limited to, strains of *Acremonium, Agaricus, Aspergillus, Aureobasidium, Chrysosporium, Coprinus, Cryptococcus, Filibasidium, Fusarium, Geosmithia, Humicola, Magnaporthe, Mucor, Myceliophthora, Neocallimastix, Neurospora, Paecilomyces, Penicillium, Piromyces, Panerochaete, Pleurotus, Rasamsonia, Schizophyllum, Talaromyces, Thermoascus, Thermomyces, Thielavia, Tolypocladium*, and *Trichoderma*.

Several strains of filamentous fungi are readily accessible to the public in a number of culture collections, such as the American Type Culture Collection (ATCC), Deutsche Sammlung von Mikroorganismen and Zellkulturen GmbH (DSM), Centraalbureau Voor Schimmelcultures (CBS), and Agricultural Research Service Patent Culture Collection, Northern Regional Research Center (NRRL). Examples of such strains include *Aspergillus niger* CBS 513.88, *Aspergillus oryzae* ATCC 20423, IFO 4177, ATCC 1011, ATCC 9576, ATCC14488-14491, ATCC 11601, ATCC12892, *P. chrysogenum* CBS 455.95, *Penicillium citrinum* ATCC 38065, *Penicillium chrysogenum* P2, *Talaromyces emersonii* CBS 393.64, *Acremonium chrysogenum* ATCC 36225 or ATCC 48272, *Trichoderma reesei* ATCC 26921 or ATCC 56765 or ATCC 26921, *Aspergillus sojae* ATCC11906, *Chrysosporium lucknowense* C1, Garg 27K, VKM F-3500-D, ATCC44006 and derivatives thereof.

An advantage of expression and production of the enzymes (for example at least two, three or four different cellulases) in a suitable microorganism may be a high enzyme composition yield which can be used in the processes of the present invention.

In the processes of the present invention enzyme compositions are used. Preferably, the compositions are stable. "Stable enzyme compositions" as used herein means that the enzyme compositions retain activity after 30 hours of hydrolysis reaction time, preferably at least 10%, 20%, 30%, 40%, 50%, 60%, 65%, 70%, 75%, 80% 85%, 90%, 95%, 96%, 97%, 98%, 99% or 100% of its initial activity after 30 hours of hydrolysis reaction time. Preferably, the enzyme composition retains activity after 40, 50, 60, 70, 80, 90 100, 150, 200, 250, 300, 350, 400, 450, 500 hours of hydrolysis reaction time.

The enzyme composition may be prepared by fermentation of a suitable substrate with a suitable microorganism, e.g. *Rasamsonia emersonii* or *Aspergillus niger*, wherein the enzyme composition is produced by the microorganism. The microorganism may be altered to improve or to make the composition. For example, the microorganism may be mutated by classical strain improvement procedures or by recombinant DNA techniques. Therefore, the microorganisms mentioned herein can be used as such to produce the composition or may be altered to increase the production or to produce an altered composition which might include heterologous enzymes, e.g. cellulases, thus enzymes that are not originally produced by that microorganism. Preferably, a fungus, more preferably a filamentous fungus is used to produce the composition. Advantageously, a thermophilic or thermotolerant microorganism is used. Optionally, a substrate is used that induces the expression of the enzymes in the enzyme composition during the production of the enzyme composition.

The enzyme composition is used to release sugars from lignocellulosic material, that comprises polysaccharides. The major polysaccharides are cellulose (glucans), hemicelluloses (xylans, heteroxylans and xyloglucans). In addition, some hemicellulose may be present as glucomannans, for example in wood-derived lignocellulosic material. The enzymatic hydrolysis of these polysaccharides to soluble sugars, including both monomers and multimers, for example glucose, cellobiose, xylose, arabinose, galactose, fructose, mannose, rhamnose, ribose, galacturonic acid, glucoronic acid and other hexoses and pentoses occurs under the action of different enzymes acting in concert. By sugar product is meant the enzymatic hydrolysis product of the lignocellulosic material. The sugar product comprises soluble sugars, including both monomers and multimers. Preferably, it comprises glucose. Examples of other sugars are cellobiose, xylose, arabinose, galactose, fructose, mannose, rhamnose, ribose, galacturonic acid, glucoronic acid and other hexoses and pentoses. The sugar product may be used as such or may be further processed for example recovered and/or purified.

In addition, pectins and other pectic substances such as arabinans may make up considerably proportion of the dry mass of typically cell walls from non-woody plant tissues (about a quarter to half of dry mass may be pectins).

Cellulose is a linear polysaccharide composed of glucose residues linked by β-1,4 bonds. The linear nature of the cellulose fibers, as well as the stoichiometry of the β-linked glucose (relative to α) generates structures more prone to inter strand hydrogen bonding than the highly branched α-linked structures of starch. Thus, cellulose polymers are generally less soluble and form more tightly bound fibers than the fibers found in starch.

Enzymes that may be included in the stable enzyme composition used in the invention are described in more detail below.

Lytic polysaccharide monooxygenases, endoglucanases (EG) and exo-cellobiohydrolases (CBH) catalyze the hydrolysis of insoluble cellulose to products such as cellooligosaccharides (cellobiose as a main product), while β-glucosidases (BG) convert the oligosaccharides, mainly cellobiose and cellotriose, to glucose.

Hemicellulose is a complex polymer, and its composition often varies widely from organism to organism and from one tissue type to another. In general, a main component of hemicellulose is β-1,4-linked xylose, a five carbon sugar. However, this xylose is often branched at 0 to 3 and/or 0 to 2 atoms of xylose, and can be substituted with linkages to arabinose, galactose, mannose, glucuronic acid, galacturonic acid or by esterification to acetic acid (and esterification of ferulic acid to arabinose). Hemicellulose can also contain glucan, which is a general term for β-linked six carbon sugars (such as the β-(1,3)(1,4) glucans and heteroglucans mentioned previously) and additionally glucomannans (in which both glucose and mannose are present in the linear backbone, linked to each other by β-linkages).

Xylanases together with other accessory enzymes, for example α-L-arabinofuranosidases, feruloyl and acetylxylan esterases, glucuronidases, and β-xylosidases) catalyze the hydrolysis of hemicellulose.

Pectic substances include pectins, arabinans, galactans and arabinogalactans. Pectins are the most complex polysaccharides in the plant cell wall. They are built up around a core chain of α(1,4)-linked D-galacturonic acid units interspersed to some degree with L-rhamnose. In any one cell wall there are a number of structural units that fit this description and it has generally been considered that in a single pectic molecule, the core chains of different structural units are continuous with one another. The principal types of structural unit are: galacturonan (homogalacturonan), which may be substituted with methanol on the carboxyl group and acetate on O-2 and O-3; rhamnogalacturonan I (RGI), in which galacturonic acid units alternate with rhamnose units carrying (1,4)-linked galactan and (1,5)-linked arabinan side-chains. The arabinan side-chains may be attached directly to rhamnose or indirectly through the galactan chains; xylogalacturonan, with single xylosyl units on 0-3 of galacturonic acid (closely associated with RGI); and rhamnogalacturonan II (RGII), a particularly complex minor unit containing unusual sugars, for example apiose. An RGII unit may contain two apiosyl residues which, under suitable ionic conditions, can reversibly form esters with borate.

An enzyme composition for use in the processes of the current invention comprises preferably at least two activities, although typically a composition will comprise more than two activities, for example, three, four, five, six, seven, eight, nine or even more activities. Typically, an enzyme composition for use in the processes of the current invention comprises at least two cellulases. The at least two cellulases may contain the same or different activities. The enzyme composition for use in the processes of the current invention may also comprises at least one enzyme other than a cellulase. Preferably, the at least one other enzyme has an auxiliary enzyme activity, i.e. an additional activity which, either directly or indirectly leads to lignocellulose degradation. Examples of such auxiliary activities are mentioned herein and include, but are not limited to hemicellulases.

Thus, a composition for use in the processes of the current invention may comprise lytic polysaccharide monooxygenase activity, endoglucanase activity and/or cellobiohydrolase activity and/or β-glucosidase activity. A composition for use in the invention may comprise more than one enzyme activity per activity class. For example, a composition for use in the invention may comprise two endoglucanase activities, for example, endo-1,3(1,4)-β glucanase activity and endo-β-1,4-glucanase activity.

A composition for use in the processes of the current invention may be derived from *Rasamsonia emersonii*. In the invention, it is anticipated that a core set of (lignocellulose degrading) enzyme activities may be derived from *Rasamsonia emersonii*. *Rasamsonia emersonii* can provide a highly effective set of activities as demonstrated herein for the hydrolysis of lignocellulosic material. If needed, the set of activities can be supplemented with additional enzyme activities from other sources. Such additional activities may be derived from classical sources and/or produced by a genetically modified organisms.

The activities in a composition for use in the processes of the current invention may be thermostable. Herein, this means that the activity has a temperature optimum of 60° C. or higher, 70° C. or higher, 75° C. or higher, 80° C. or higher, 85° C. or higher. Activities in a composition for use in the processes of the current invention will typically not have the same temperature optima, but preferably will, nevertheless, be thermostable.

In addition, enzyme activities in a composition for use in the processes of the current invention may be able to work at low pH. For the purposes of this invention, low pH indicates a pH of 5.5 or lower, 5 or lower, 4.9 or lower, 4.8 or lower, 4.7 or lower, 4.6 or lower, 4.5 or lower, 4.4 or lower, 4.3 or lower, 4.2 or lower, 4.1 or lower, 4.0 or lower 3.9 or lower, 3.8 or lower, 3.7 or lower, 3.6 or lower, 3.5 or lower.

Activities in a composition for use in the processes of the current invention may be defined by a combination of any of the above temperature optima and pH values.

The enzyme composition for use in the processes of the current invention may comprise, in addition to the activities derived from *Rasamsonia*, a cellulase (for example one derived from a source other than *Rasamsonia*) and/or a hemicellulase (for example one derived from a source other than *Rasamsonia*) and/or a pectinase.

An enzyme composition for use in the processes of the current invention may comprise one, two, three, four classes or more of cellulase, for example one, two, three or four or all of a lytic polysaccharide monooxygenas (LPMO), an endoglucanase (EG), one or two exo-cellobiohydrolase (CBH) and a β-glucosidase (BG). A composition for use in the processes of the current invention may comprise two or more of any of these classes of cellulase.

An enzyme composition for use in the processes of the current invention may comprise one type of cellulase activity and/or hemicellulase activity and/or pectinase activity provided by a composition as described herein and a second type of cellulase activity and/or hemicellulase activity and/or pectinase activity provided by an additional cellulose/hemicellulase/pectinase.

As used herein, a cellulase is any polypeptide which is capable of degrading or modifying cellulose. A polypeptide which is capable of degrading cellulose is one which is capable of catalysing the process of breaking down cellulose into smaller units, either partially, for example into cellodextrins, or completely into glucose monomers. A cellulase according to the invention may give rise to a mixed population of cellodextrins and glucose monomers. Such degradation will typically take place by way of a hydrolysis reaction.

Lytic polysaccharide monooxygenases (LPMO) are recently classified by CAZy in family AA9 (Auxiliary Activity Family 9) or family AA10 (Auxiliary Activity Family 10). As mentioned above, lytic polysaccharide monooxygenases are able to open a crystalline glucan structure. Lytic polysaccharide monooxygenases may also affect cellooligosaccharides. GH61 (glycoside hydrolase family 61 or sometimes referred to EGIV) proteins are (lytic) oxygen-dependent polysaccharide monooxygenases (PMO's/LPMO's) according to the latest literature (see Isaksen et al., Journal of Biological Chemistry, vol. 289, no. 5, pp. 2632-2642). PMO and LPMO are used herein interchangeably. Often in literature these proteins are mentioned to enhance the action of cellulases on lignocellulose substrates. GH61 was originally classified as endoglucanase based on measurement of very weak endo-1,4-β-d-glucanase activity in one family member. The term "GH61" as used herein, is to be understood as a family of enzymes, which share common conserved sequence portions and folding to be classified in family 61 of the well-established CAZy GH classification system (cazy.org/GH61.html). The glycoside hydrolase family 61 is a member of the family of glycoside hydrolases EC 3.2.1. GH61 are recently now reclassified by CAZy in family AA9 (Auxiliary Activity Family 9). GH61 is used herein as being part of the cellulases.

CBM33 (family 33 carbohydrate-binding module) is a lytic polysaccharide monooxygenase (see Isaksen et al, Journal of Biological Chemistry, vol. 289, no. 5, pp. 2632-2642), CAZy has recently reclassified CBM33 in AA10 (Auxiliary Activity Family 10).

As used herein, a hemicellulase is any polypeptide which is capable of degrading or modifying hemicellulose. That is to say, a hemicellulase may be capable of degrading or modifying one or more of xylan, glucuronoxylan, arabinoxylan, glucomannan and xyloglucan. A polypeptide which is capable of degrading a hemicellulose is one which is capable of catalysing the process of breaking down the hemicellulose into smaller polysaccharides, either partially, for example into oligosaccharides, or completely into sugar monomers, for example hexose or pentose sugar monomers. A hemicellulase according to the invention may give rise to a mixed population of oligosaccharides and sugar monomers. Such degradation will typically take place by way of a hydrolysis reaction.

As used herein, a pectinase is any polypeptide which is capable of degrading or modifying pectin. A polypeptide which is capable of degrading pectin is one which is capable of catalysing the process of breaking down pectin into smaller units, either partially, for example into oligosaccharides, or completely into sugar monomers. A pectinase according to the invention may give rise to a mixed population of oligosaccharides and sugar monomers. Such degradation will typically take place by way of a hydrolysis reaction.

Accordingly, an enzyme composition for use in the processes of the current invention may comprise any cellulase, for example, a lytic polysaccharide monooxygenase (e.g. GH61), a cellobiohydrolase, an endo-β-1,4-glucanase, a β-glucosidase or a β-(1,3)(1,4)-glucanase.

As used herein, a cellobiohydrolase (EC 3.2.1.91) is any polypeptide which is capable of catalysing the hydrolysis of 1,4-β-D-glucosidic linkages in cellulose or cellotetraose, releasing cellobiose from the ends of the chains. This enzyme may also be referred to as cellulase 1,4-β-cellobiosidase, 1,4-β-cellobiohydrolase, 1,4-β-D-glucan cellobiohydrolase, avicelase, exo-1,4-β-D-glucanase, exocellobiohydrolase or exoglucanase.

As used herein, an endo-β-1,4-glucanase (EC 3.2.1.4) is any polypeptide which is capable of catalysing the endohydrolysis of 1,4-β-D-glucosidic linkages in cellulose, lichenin or cereal β-D-glucans. Such a polypeptide may also be capable of hydrolyzing 1,4-linkages in β-D-glucans also containing 1,3-linkages. This enzyme may also be referred to as cellulase, avicelase, β-1,4-endoglucan hydrolase, β-1,4-glucanase, carboxymethyl cellulase, celludextrinase, endo-1,4-β-D-glucanase, endo-1,4-β-D-glucanohydrolase, endo-1,4-β-glucanase or endoglucanase.

As used herein, a β-glucosidase (EC 3.2.1.21) is any polypeptide which is capable of catalysing the hydrolysis of terminal, non-reducing β-D-glucose residues with release of β-D-glucose. Such a polypeptide may have a wide specificity for β-D-glucosides and may also hydrolyze one or more of the following: a β-D-galactoside, an α-L-arabinoside, a β-D-xyloside or a β-D-fucoside. This enzyme may also be referred to as amygdalose, β-D-glucoside glucohydrolase, cellobiase or gentobiase.

As used herein, a β-(1,3)(1,4)-glucanase (EC 3.2.1.73) is any polypeptide which is capable of catalysing the hydrolysis of 1,4-β-D-glucosidic linkages in β-D-glucans containing 1,3- and 1,4-bonds. Such a polypeptide may act on lichenin and cereal β-D-glucans, but not on β-D-glucans containing only 1,3- or 1,4-bonds. This enzyme may also be referred to as licheninase, 1,3-1,4-β-D-glucan 4-glucanohydrolase, β-glucanase, endo-β-1,3-1,4 glucanase, lichenase or mixed linkage β-glucanase. An alternative for this type of enzyme is EC 3.2.1.6, which is described as endo-1,3(4)-beta-glucanase. This type of enzyme hydrolyses 1,3- or 1,4-linkages in beta-D-glucanase when the glucose residue whose reducing group is involved in the linkage to be hydrolysed is itself substituted at C-3. Alternative names include endo-1,3-beta-glucanase, laminarinase, 1,3-(1,3;1, 4)-beta-D-glucan 3 (4) glucanohydrolase. Substrates include laminarin, lichenin and cereal beta-D-glucans.

A composition for use in the processes of the current invention may comprise any hemicellulase, for example, an endoxylanase, a β-xylosidase, a α-L-arabionofuranosidase, an α-D-glucuronidase, an acetyl xylan esterase, a feruloyl esterase, a coumaroyl esterase, an α-galactosidase, a β-galactosidase, a β-mannanase or a β-mannosidase.

As used herein, an endoxylanase (EC 3.2.1.8) is any polypeptide which is capable of catalysing the endohydrolysis of 1,4-β-D-xylosidic linkages in xylans. This enzyme may also be referred to as endo-1,4-β-xylanase or 1,4-β-D-xylan xylanohydrolase. An alternative is EC 3.2.1.136, a glucuronoarabinoxylan endoxylanase, an enzyme that is able to hydrolyze 1,4 xylosidic linkages in glucuronoarabinoxylans.

As used herein, a β-xylosidase (EC 3.2.1.37) is any polypeptide which is capable of catalysing the hydrolysis of 1,4-β-D-xylans, to remove successive D-xylose residues from the non-reducing termini. Such enzymes may also hydrolyze xylobiose. This enzyme may also be referred to as xylan 1,4-β-xylosidase, 1,4-β-D-xylan xylohydrolase, exo-1,4-β-xylosidase or xylobiase.

As used herein, an α-L-arabinofuranosidase (EC 3.2.1.55) is any polypeptide which is capable of acting on α-L-arabinofuranosides, α-L-arabinans containing (1,2) and/or (1,3)- and/or (1,5)-linkages, arabinoxylans and arabinogalactans. This enzyme may also be referred to as α-N-arabinofuranosidase, arabinofuranosidase or arabinosidase.

As used herein, an α-D-glucuronidase (EC 3.2.1.139) is any polypeptide which is capable of catalysing a reaction of the following form: alpha-D-glucuronoside+H(2)O=an alcohol+D-glucuronate. This enzyme may also be referred to as alpha-glucuronidase or alpha-glucosiduronase. These enzymes may also hydrolyse 4-O-methylated glucoronic acid, which can also be present as a substituent in xylans. An alternative is EC 3.2.1.131: xylan alpha-1,2-glucuronosidase, which catalyses the hydrolysis of alpha-1,2-(4-O-methyl)glucuronosyl links.

As used herein, an acetyl xylan esterase (EC 3.1.1.72) is any polypeptide which is capable of catalysing the deacetylation of xylans and xylo-oligosaccharides. Such a polypeptide may catalyze the hydrolysis of acetyl groups from polymeric xylan, acetylated xylose, acetylated glucose, alpha-napthyl acetate or p-nitrophenyl acetate but, typically, not from triacetylglycerol. Such a polypeptide typically does not act on acetylated mannan or pectin.

As used herein, a feruloyl esterase (EC 3.1.1.73) is any polypeptide which is capable of catalysing a reaction of the form: feruloyl-saccharide+H(2)O=ferulate+saccharide. The saccharide may be, for example, an oligosaccharide or a polysaccharide. It may typically catalyse the hydrolysis of the 4-hydroxy-3-methoxycinnamoyl (feruloyl) group from an esterified sugar, which is usually arabinose in 'natural' substrates. p-nitrophenol acetate and methyl ferulate are typically poorer substrates. This enzyme may also be referred to as cinnamoyl ester hydrolase, ferulic acid esterase or hydroxycinnamoyl esterase. It may also be referred to as a hemicellulase accessory enzyme, since it may help xylanases and pectinases to break down plant cell wall hemicellulose and pectin.

As used herein, a coumaroyl esterase (EC 3.1.1.73) is any polypeptide which is capable of catalysing a reaction of the form: coumaroyl-saccharide+H(2)O=coumarate+saccharide. The saccharide may be, for example, an oligosaccharide or a polysaccharide. This enzyme may also be referred to as trans-4-coumaroyl esterase, trans-p-coumaroyl esterase, p-coumaroyl esterase or p-coumaric acid esterase. This enzyme also falls within EC 3.1.1.73 so may also be referred to as a feruloyl esterase.

As used herein, an α-galactosidase (EC 3.2.1.22) is any polypeptide which is capable of catalysing the hydrolysis of terminal, non-reducing α-D-galactose residues in α-D-galactosides, including galactose oligosaccharides, galactomannans, galactans and arabinogalactans. Such a polypeptide may also be capable of hydrolyzing α-D-fucosides. This enzyme may also be referred to as melibiase.

As used herein, a β-galactosidase (EC 3.2.1.23) is any polypeptide which is capable of catalysing the hydrolysis of terminal non-reducing β-D-galactose residues in β-D-galactosides. Such a polypeptide may also be capable of hydrolyzing α-L-arabinosides. This enzyme may also be referred to as exo-(1->4)-β-D-galactanase or lactase.

As used herein, a β-mannanase (EC 3.2.1.78) is any polypeptide which is capable of catalysing the random hydrolysis of 1,4-β-D-mannosidic linkages in mannans, galactomannans and glucomannans. This enzyme may also be referred to as mannan endo-1,4-β-mannosidase or endo-1,4-mannanase.

As used herein, a β-mannosidase (EC 3.2.1.25) is any polypeptide which is capable of catalysing the hydrolysis of terminal, non-reducing β-D-mannose residues in β-D-mannosides. This enzyme may also be referred to as mannanase or mannase.

A composition for use in the processes of the current invention may comprise any pectinase, for example an endo polygalacturonase, a pectin methyl esterase, an endo-galactanase, a beta galactosidase, a pectin acetyl esterase, an endo-pectin lyase, pectate lyase, alpha rhamnosidase, an exo-galacturonase, an expolygalacturonate lyase, a rhamnogalacturonan hydrolase, a rhamnogalacturonan lyase, a rhamnogalacturonan acetyl esterase, a rhamnogalacturonan galacturonohydrolase, a xylogalacturonase.

As used herein, an endo-polygalacturonase (EC 3.2.1.15) is any polypeptide which is capable of catalysing the random hydrolysis of 1,4-α-D-galactosiduronic linkages in pectate and other galacturonans. This enzyme may also be referred to as polygalacturonase pectin depolymerase, pectinase, endopolygalacturonase, pectolase, pectin hydrolase, pectin polygalacturonase, poly-α-1,4-galacturonide glycanohydrolase, endogalacturonase; endo-D-galacturonase or poly(1,4-α-D-galacturonide) glycanohydrolase.

As used herein, a pectin methyl esterase (EC 3.1.1.11) is any enzyme which is capable of catalysing the reaction: pectin+n H$_2$O=n methanol+pectate. The enzyme may also been known as pectinesterase, pectin demethoxylase, pectin methoxylase, pectin methylesterase, pectase, pectinoesterase or pectin pectylhydrolase.

As used herein, an endo-galactanase (EC 3.2.1.89) is any enzyme capable of catalysing the endohydrolysis of 1,4-β-D-galactosidic linkages in arabinogalactans. The enzyme may also be known as arabinogalactan endo-1,4-β-galactosidase, endo-1,4-β-galactanase, galactanase, arabinogalactanase or arabinogalactan 4-β-D-galactanohydrolase.

As used herein, a pectin acetyl esterase is defined herein as any enzyme which has an acetyl esterase activity which catalyses the deacetylation of the acetyl groups at the hydroxyl groups of GalUA residues of pectin.

As used herein, an endo-pectin lyase (EC 4.2.2.10) is any enzyme capable of catalysing the eliminative cleavage of (1→4)-α-D-galacturonan methyl ester to give oligosaccharides with 4-deoxy-6-O-methyl-α-D-galact-4-enuronosyl groups at their non-reducing ends. The enzyme may also be known as pectin lyase, pectin trans-eliminase; endo-pectin lyase, polymethylgalacturonic transeliminase, pectin methyltranseliminase, pectolyase, PL, PNL or PMGL or (1→4)-6-O-methyl-α-D-galacturonan lyase.

As used herein, a pectate lyase (EC 4.2.2.2) is any enzyme capable of catalysing the eliminative cleavage of (1→4)-α-D-galacturonan to give oligosaccharides with 4-deoxy-α-D- galact-4-enuronosyl groups at their non-reducing ends. The enzyme may also be known polygalacturonic transeliminase, pectic acid transeliminase, polygalacturonate lyase, endopectin methyltranseliminase, pectate transeliminase, endogalacturonate transeliminase, pectic acid lyase, pectic lyase, α-1,4-D-endopolygalacturonic acid lyase, PGA lyase, PPase-N, endo-α-1,4-polygalacturonic acid lyase, polygalacturonic acid lyase, pectin trans-eliminase, polygalacturonic acid trans-eliminase or (1→4)-α-D-galacturonan lyase.

As used herein, an alpha rhamnosidase (EC 3.2.1.40) is any polypeptide which is capable of catalysing the hydrolysis of terminal non-reducing α-L-rhamnose residues in α-L-rhamnosides or alternatively in rhamnogalacturonan. This enzyme may also be known as α-L-rhamnosidase T, α-L-rhamnosidase N or α-L-rhamnoside rhamnohydrolase.

As used herein, exo-galacturonase (EC 3.2.1.82) is any polypeptide capable of hydrolysis of pectic acid from the non-reducing end, releasing digalacturonate. The enzyme may also be known as exo-poly-α-galacturonosidase, exopolygalacturonosidase or exopolygalacturanosidase.

As used herein, exo-galacturonase (EC 3.2.1.67) is any polypeptide capable of catalysing: $(1,4-\alpha-D-galacturonide)_n + H_2O = (1,4-\alpha-D-galacturonide)_{n-1} + D$-galacturonate. The enzyme may also be known as galacturan 1,4-α-galacturonidase, exopolygalacturonase, poly(galacturonate) hydrolase, exo-D-galacturonase, exo-D-galacturonanase, exopoly-D-galacturonase or poly(1,4-α-D-galacturonide) galacturonohydrolase.

As used herein, exopolygalacturonate lyase (EC 4.2.2.9) is any polypeptide capable of catalysing eliminative cleavage of 4-(4-deoxy-α-D-galact-4-enuronosyl)-D-galacturonate from the reducing end of pectate, i.e. de-esterified pectin. This enzyme may be known as pectate disaccharide-lyase, pectate exo-lyase, exopectic acid transeliminase, exopectate lyase, exopolygalacturonic acid-trans-eliminase, PATE, exo-PATE, exo-PGL or (1→4)-α-D-galacturonan reducing-end-disaccharide-lyase.

As used herein, rhamnogalacturonan hydrolase is any polypeptide which is capable of hydrolyzing the linkage between galactosyluronic acid and rhamnopyranosyl in an endo-fashion in strictly alternating rhamnogalacturonan structures, consisting of the disaccharide [(1,2-alpha-L-rhamnoyl-(1,4)-alpha-galactosyluronic acid].

As used herein, rhamnogalacturonan lyase is any polypeptide which is any polypeptide which is capable of cleaving α-L-Rhap-(1→4)-α-D-GalpA linkages in an endo-fashion in rhamnogalacturonan by beta-elimination.

As used herein, rhamnogalacturonan acetyl esterase is any polypeptide which catalyzes the deacetylation of the backbone of alternating rhamnose and galacturonic acid residues in rhamnogalacturonan.

As used herein, rhamnogalacturonan galacturonohydrolase is any polypeptide which is capable of hydrolyzing galacturonic acid from the non-reducing end of strictly alternating rhamnogalacturonan structures in an exo-fashion.

As used herein, xylogalacturonase is any polypeptide which acts on xylogalacturonan by cleaving the β-xylose substituted galacturonic acid backbone in an endo-manner. This enzyme may also be known as xylogalacturonan hydrolase.

As used herein, an α-L-arabinofuranosidase (EC 3.2.1.55) is any polypeptide which is capable of acting on α-L-arabinofuranosides, α-L-arabinans containing (1,2) and/or (1,3)- and/or (1,5)-linkages, arabinoxylans and arabinogalactans. This enzyme may also be referred to as α-N-arabinofuranosidase, arabinofuranosidase or arabinosidase.

As used herein, endo-arabinanase (EC 3.2.1.99) is any polypeptide which is capable of catalysing endohydrolysis of 1,5-α-arabinofuranosidic linkages in 1,5-arabinans. The enzyme may also be known as endo-arabinase, arabinan endo-1,5-α-L-arabinosidase, endo-1,5-α-L-arabinanase, endo-α-1,5-arabanase; endo-arabanase or 1,5-α-L-arabinan 1,5-α-L-arabinanohydrolase.

An enzyme composition for use in the processes of the current invention will typically comprise at least two cellulases and optionally at least one hemicellulase and optionally at least one pectinase. A composition for use in the processes of the current invention may comprise a GH61, a cellobiohydrolase, an endoglucanase and/or a β-glucosidase. Such a composition may also comprise one or more hemicellulases and/or one or more pectinases.

In addition, one or more (for example two, three, four or all) of an amylase, a protease, a lipase, a ligninase, a hexosyltransferase, a glucuronidase, an expansin, a cellulose induced protein or a cellulose integrating protein or like protein may be present in a composition for use in the processes of the current invention (these are referred to as auxiliary activities above).

"Protease" includes enzymes that hydrolyze peptide bonds (peptidases), as well as enzymes that hydrolyze bonds between peptides and other moieties, such as sugars (glycopeptidases). Many proteases are characterized under EC 3.4 and are suitable for use in the processes of the current invention. Some specific types of proteases include, cysteine proteases including pepsin, papain and serine proteases including chymotrypsins, carboxypeptidases and metalloendopeptidases.

"Lipase" includes enzymes that hydrolyze lipids, fatty acids, and acylglycerides, including phosphoglycerides, lipoproteins, diacylglycerols, and the like. In plants, lipids are used as structural components to limit water loss and pathogen infection. These lipids include waxes derived from fatty acids, as well as cutin and suberin.

"Ligninase" includes enzymes that can hydrolyze or break down the structure of lignin polymers. Enzymes that can break down lignin include lignin peroxidases, manganese peroxidases, laccases and feruloyl esterases, and other enzymes described in the art known to depolymerize or otherwise break lignin polymers. Also included are enzymes capable of hydrolyzing bonds formed between hemicellulosic sugars (notably arabinose) and lignin. Ligninases include but are not limited to the following group of enzymes: lignin peroxidases (EC 1.11.1.14), manganese peroxidases (EC 1.11.1.13), laccases (EC 1.10.3.2) and feruloyl esterases (EC 3.1.1.73).

"Hexosyltransferase" (2.4.1-) includes enzymes which are capable of catalysing a transferase reaction, but which can also catalyze a hydrolysis reaction, for example of cellulose and/or cellulose degradation products. An example of a hexosyltransferase which may be used in the invention is a β-glucanosyltransferase. Such an enzyme may be able to catalyze degradation of (1,3)(1,4)glucan and/or cellulose and/or a cellulose degradation product.

"Glucuronidase" includes enzymes that catalyze the hydrolysis of a glucoronoside, for example β-glucuronoside to yield an alcohol. Many glucuronidases have been characterized and may be suitable for use in the invention, for example β-glucuronidase (EC 3.2.1.31), hyalurono-glucuronidase (EC 3.2.1.36), glucuronosyl-disulfoglucosamine glucuronidase (3.2.1.56), glycyrrhizinate β-glucuronidase (3.2.1.128) or α-D-glucuronidase (EC 3.2.1.139).

A composition for use in the processes of the current invention may comprise an expansin or expansin-like protein, such as a swollenin (see Salheimo et al., Eur. J. Biochem. 269, 4202-4211, 2002) or a swollenin-like protein.

Expansins are implicated in loosening of the cell wall structure during plant cell growth. Expansins have been proposed to disrupt hydrogen bonding between cellulose and other cell wall polysaccharides without having hydrolytic activity. In this way, they are thought to allow the sliding of cellulose fibers and enlargement of the cell wall. Swollenin, an expansin-like protein contains an N-terminal Carbohydrate Binding Module Family 1 domain (CBD) and a C-terminal expansin-like domain. For the purposes of this invention, an expansin-like protein or swollenin-like protein may comprise one or both of such domains and/or may disrupt the structure of cell walls (such as disrupting cellulose structure), optionally without producing detectable amounts of reducing sugars.

A composition for use in the processes of the current invention may be a cellulose induced protein, for example the polypeptide product of the cip1 or cip2 gene or similar genes (see Foreman et al., J. Biol. Chem. 278(34), 31988-31997, 2003), a cellulose/cellulosome integrating protein, for example the polypeptide product of the cipA or cipC gene, or a scaffoldin or a scaffoldin-like protein. Scaffoldins and cellulose integrating proteins are multi-functional integrating subunits which may organize cellulolytic subunits into a multi-enzyme complex. This is accomplished by the interaction of two complementary classes of domain, i.e. a cohesion domain on scaffoldin and a dockerin domain on each enzymatic unit. The scaffoldin subunit also bears a cellulose-binding module (CBM) that mediates attachment of the cellulosome to its substrate. A scaffoldin or cellulose integrating protein for the purposes of this invention may comprise one or both of such domains.

A composition for use in the processes of the current invention may be composed of a member of each of the classes of enzymes mentioned above, several members of one enzyme class, or any combination of these enzymes classes or helper proteins (i.e. those proteins mentioned herein which do not have enzymatic activity per se, but do nevertheless assist in lignocellulosic degradation).

A composition for use in the processes of the current invention may be composed of enzymes from (1) commercial suppliers; (2) cloned genes expressing enzymes; (3) broth (such as that resulting from growth of a microbial strain in media, wherein the strains secrete proteins and enzymes into the media; (4) cell lysates of strains grown as in (3); and/or (5) plant material expressing enzymes. Different enzymes in a composition of the invention may be obtained from different sources.

The enzymes can be produced either exogenously in microorganisms, yeasts, fungi, bacteria or plants, then isolated and added, for example, to lignocellulosic material. Alternatively, the enzyme may be produced in a fermentation that uses (pretreated) lignocellulosic material (such as corn stover or wheat straw) to provide nutrition to an organism that produces an enzyme(s). In this manner, plants that produce the enzymes may themselves serve as a lignocellulosic material and be added into lignocellulosic material.

In the uses and methods described herein, the components of the compositions described above may be provided concomitantly (i.e. as a single composition per se) or separately or sequentially.

In an embodiment the enzyme compositions for use in the processes of the current invention may be a whole fermentation broth as described below. The whole fermentation broth may comprise any of the above-mentioned polypeptides or any combination thereof. Preferably, the enzyme composition is whole fermentation broth wherein the cells are killed. The whole fermentation broth may contain organic acid(s) (used for killing the cells), killed cells and/or cell debris, and culture medium. In an embodiment, the whole fermentation broth comprises a first organic acid component comprising at least one 1-5 carbon organic acid and/or a salt thereof and a second organic acid component comprising at least 6 or more carbon organic acid and/or a salt thereof. In an embodiment, the first organic acid component is acetic acid, formic acid, propionic acid, a salt thereof, or any combination thereof and the second organic acid component is benzoic acid, cyclohexanecarboxylic acid, 4-methylvaleric acid, phenylacetic acid, a salt thereof, or any combination thereof.

The term "whole fermentation broth" as used herein refers to a preparation produced by cellular fermentation that undergoes no or minimal recovery and/or purification. For example, whole fermentation broths are produced when microbial cultures are grown to saturation, incubated under carbon-limiting conditions to allow protein synthesis (e.g., expression of enzymes by host cells) and secretion into cell culture medium. Typically, the whole fermentation broth is unfractionated and comprises spent cell culture medium, extracellular enzymes, and microbial, preferably nonviable, cells.

If needed, the whole fermentation broth can be fractionated and the one or more of the fractionated contents can be used. For instance, the killed cells and/or cell debris can be removed from a whole fermentation broth to provide a composition that is free of these components.

The whole fermentation broth may further comprise a preservative and/or anti-microbial agent. Such preservatives and/or agents are known in the art.

The whole fermentation broth as described herein is typically a liquid, but may contain insoluble components, such as killed cells, cell debris, culture media components, and/or insoluble enzyme(s). In some embodiments, insoluble components may be removed to provide a clarified whole fermentation broth.

As described above, an enzyme composition is present in step (d) and in step (f) of the processes of the current invention. These enzyme compositions may be the same or may be different. Furthermore, as described above, additional enzymes are added during step (d) and/or step (f) of the processes according to the present invention. The enzymes added may be enzymes that are already present in step (d) and step (f). Alternatively, they may be different enzymes. Moreover, the additional enzymes added during step (d) may differ or may be the same as the additional enzymes added during step (f) of the processes according to the present invention.

Lignocellulosic material as used herein includes any lignocellulosic and/or hemicellulosic material. Lignocellulosic material suitable for use in the processes of the current invention includes biomass, e.g. virgin biomass and/or non-virgin biomass such as agricultural biomass, commercial organics, construction and demolition debris, municipal solid waste, waste paper and yard waste. Common forms of biomass include trees, shrubs and grasses, wheat, wheat straw, sugar cane bagasse, switch grass, miscanthus, energy cane, corn, corn stover, corn husks, corn cobs, canola stems, soybean stems, sweet sorghum, corn kernel including fiber from kernels, products and by-products from milling of grains such as corn, wheat and barley (including wet milling and dry milling) often called "bran or fibre" as well as municipal solid waste, waste paper and yard waste. The biomass can also be, but is not limited to, herbaceous material, agricultural residues, forestry residues, municipal solid wastes, waste paper, and pulp and paper mill residues. "Agricultural biomass" includes branches, bushes, canes, corn and corn husks, energy crops, forests, fruits, flowers, grains, grasses, herbaceous crops, leaves, bark, needles, logs, roots, saplings, short rotation woody crops, shrubs, switch grasses, trees, vegetables, fruit peels, vines, sugar beet pulp, wheat midlings, oat hulls, and hard and soft woods (not including woods with deleterious materials). In addition, agricultural biomass includes organic waste materials generated from agricultural processes including farming and forestry activities, specifically including forestry wood waste. Agricultural biomass may be any of the aforementioned singularly or in any combination or mixture thereof.

Cellulose is an organic compound with the formula $(C_6H_{10}O_5)_n$, a polysaccharide consisting of a linear chain of several hundred to over ten thousand $\beta(1\rightarrow 4)$ linked D-glucose units. A glucan molecule is a polysaccharide of D-glucose monomers linked by glycosidic bonds. Herein glucan and cellulose are used interchangeably for a polysaccharide of D-glucose monomers linked by glycosidic bonds. Methods for the quantitative analysis of glucan or polysaccharide compositions are well-known and described in the art and are for example summarized in Carvalho de Souza et al., Carbohydrate Polymers 95 (2013) 657-663. In general, 50 to 70% of the glucan is crystalline cellulose, the remainder is amorphous cellulose.

As described above, the lignocellulosic material may optionally be pretreated. Pretreatment methods are known in the art and include, but are not limited to, heat, mechanical, chemical modification, biological modification and any combination thereof. Pretreatment is typically performed in order to enhance the accessibility of the lignocellulosic material to enzymatic hydrolysis and/or hydrolyse the hemicellulose and/or solubilize the hemicellulose and/or cellulose and/or lignin, in the lignocellulosic material. In an embodiment, the pretreatment comprises treating the lignocellulosic material with steam explosion, hot water treatment or treatment with dilute acid or dilute base.

As described above, the lignocellulosic material may optionally be washed. The optional washing step may be used to remove water soluble compounds that may act as inhibitors for the fermentation and/or hydrolysis step. The washing step may be conducted in manner known to the skilled person.

The enzyme composition used in the process of the invention can extremely effectively hydrolyze lignocellulosic material, for example corn stover or wheat straw, which can then be further converted into a product, such as ethanol, biogas, butanol, lactic acid, a plastic, an organic acid, a solvent, an animal feed supplement, a pharmaceutical, a vitamin, an amino acid, an enzyme or a chemical feedstock. Additionally, intermediate products from a process following the hydrolysis, for example lactic acid as intermediate in biogas production, can be used as building block for other materials. The present invention is exemplified with the production of ethanol but this is done as exemplification only rather than as limitation, the other products mentioned can be produced equally well.

The process according to the invention comprises two enzymatic hydrolysis steps, step (d) and step (f). In step (d) hydrolysis is mainly performed for the purpose of liquefaction of the lignocellulosic material, while in step (f) hydrolysis is mainly performed for the purpose of releasing sugar from the lignocellulosic material. Depending on the lignocellulosic material and the pretreatment method, different reaction conditions, e.g. temperature, enzyme dosage, hydrolysis reaction time and dry matter concentration, may be adapted by the skilled person in order to achieve a desired purpose of the hydrolysis. Some indications are given below.

In an embodiment the enzymatic hydrolysis in step (d) and/or step (f) of the processes according to the present invention is conducted at a temperature of 45° C. or more, 50° C. or more, 55° C. or more, 60° C. or more, 65° C. or more, or 70° C. or more. The high temperature during hydrolysis has many advantages, which include working at the optimum temperature of the enzyme composition, the reduction of risk of (bacterial) contamination, reduced viscosity, smaller amount of cooling water required, use of cooling water with a higher temperature, re-use of the enzymes and more. The temperature used in the enzymatic hydrolysis in step (d) and/or step (f) may differ or may be the same.

In an embodiment the amount of enzyme composition added (herein also called enzyme dosage or enzyme load) is low. In an embodiment the amount of enzyme is 6 mg protein/g dry matter weight or lower, 5 mg protein/g dry matter or lower, 4 mg protein/g dry matter or lower, 3 mg protein/g dry matter or lower, 2 mg protein/g dry matter or lower, or 1 mg protein/g dry matter or lower (expressed as protein in mg protein/g dry matter). In an embodiment, the amount of enzyme is 0.5 mg enzyme/g dry matter weight or lower, 0.4 mg enzyme composition/g dry matter weight or lower, 0.3 mg enzyme/g dry matter weight or lower, 0.25 mg enzyme/g dry matter weight or lower, 0.20 mg enzyme/g dry matter weight or lower, 0.18 mg enzyme/g dry matter weight or lower, 0.15 mg enzyme/g dry matter weight or lower or 0.10 mg enzyme/g dry matter weight or lower (expressed as total of cellulase enzymes in mg enzyme/g dry matter). A low enzyme dosage is possible, because of the activity and stability of the enzymes. The amount of enzyme composition added in the enzymatic hydrolysis in step (d) and/or step (f) may differ or may be the same.

In an embodiment the total hydrolysis time is 6 hours or more, 10 hours or more, 20 hours or more, 40 hours or more, 50 hours or more, 60 hours or more, 70 hours or more, 80 hours or more, 90 hours or more, 100 hours or more, 120 hours or more, 130 h or more.

In an embodiment, the total hydrolysis time is 5 to 150 hours, 30 to 140 hours, 40 to 120 hours, 45 to 110 hours, 50 to 100 hours, 55 to 95 hours, 60 to 90 hours, 65 to 85 hours or 70 to 80 hours. Due to the stability of the enzyme composition longer hydrolysis reaction times are possible with corresponding higher sugar yields. "Total hydrolysis time" as used herein means reaction time of step (d) and step (f).

In an embodiment the enzymatic hydrolysis time in step (d) of the processes according to the present invention is 3 to 30 hours.

In an embodiment the enzymatic hydrolysis time in step (f) of the processes according to the present invention is 3 to 120 hours.

The pH during hydrolysis may be chosen by the skilled person. In an embodiment the pH during the hydrolysis may be 3.0 to 6.4. The stable enzymes of the invention may have a broad pH range of up to 2 pH units, up to 3 pH units, up to 5 pH units. The optimum pH may lie within the limits of pH 2.0 to 8.0, 2.5 to 7.5, 3.0 to 7.0, 3.5 to 6.5, 4.0 to 5.0, 4.0 to 4.5 or is about 4.2. The pH used in the enzymatic hydrolysis in step (d) and/or step (f) may differ or may be the same. The optimum pH of the enzyme composition used in the enzymatic hydrolysis in step (d) and/or step (f) may differ or may be the same.

In an embodiment the hydrolysis step is conducted until 70% or more, 80% or more, 85% or more, 90% or more, 92% or more, 95% or more of available sugar in the lignocellulosic material is released.

Significantly, a process of the invention may be carried out using high levels of dry matter (of the lignocellulosic material) in the hydrolysis reaction. In an embodiment the dry matter content at the end of the hydrolysis of step (f) is 5 wt % or higher, 6 wt % or higher, 7 wt % or higher, 8 wt % or higher, 9 wt % or higher, 10 wt % or higher, 11 wt % or higher, 12 wt % or higher, 13 wt % or higher, 14 wt % or higher, 15 wt % or higher, 16 wt % or higher, 17 wt % or higher, 18 wt % or higher, 19 wt % or higher, 20 wt % or higher, 21 wt % or higher, 22 wt % or higher, 23 wt % or higher, 24 wt % or higher, 25 wt % or higher, 26 wt % or higher, 27 wt % or higher, 28 wt % or higher, 29 wt % or higher, 30 wt % or higher, 31 wt % or higher, 32 wt % or higher, 33 wt % or higher, 34 wt % or higher, 35 wt % or higher, 36 wt % or higher, 37 wt % or higher, 38 wt % or higher, 39 wt % or higher or 40 wt % or higher.

In an embodiment the fermentation in step (h) of the processes according to the present invention is performed in the second container. Ergo, the fermentation can be done simultaneously with the saccharification in one container (a process called SSF). Alternatively, the fermentation in step (h) can also be performed in a third container. Preferably, the fermentation is done after the hydrolysis and optimal conditions for both hydrolysis and fermentation can be selected which might be different for hydrolysis and fermentation. In a further aspect, the invention thus includes in step fermentation processes in which a microorganism is used for the fermentation of a carbon source comprising sugar(s), e.g. glucose, L-arabinose and/or xylose. The carbon source may include any carbohydrate oligo- or polymer comprising L-arabinose, xylose or glucose units, such as e.g. lignocellulose, xylans, cellulose, starch, arabinan and the like. For release of xylose or glucose units from such carbohydrates, appropriate carbohydrases (such as xylanases, glucanases, amylases and the like) may be added to the fermentation medium or may be produced by the modified host cell. In the latter case, the modified host cell may be genetically engineered to produce and excrete such carbohydrases. An additional advantage of using oligo- or polymeric sources of glucose is that it enables to maintain a low(er) concentration of free glucose during the fermentation, e.g. by using rate-limiting amounts of the carbohydrases. This, in turn, will prevent repression of systems required for metabolism and transport of non-glucose sugars such as xylose. In a preferred process the modified host cell ferments both the L-arabinose (optionally xylose) and glucose, preferably simultaneously in which case preferably a modified host cell is used which is insensitive to glucose repression to prevent diauxic growth. In addition to a source of L-arabinose, optionally xylose (and glucose) as carbon source, the fermentation medium will further comprise the appropriate ingredient required for growth of the modified host cell. Compositions of fermentation media for growth of microorganisms such as yeasts or filamentous fungi are well known in the art.

The fermentation time may be shorter than in conventional fermentation at the same conditions, wherein part of the enzymatic hydrolysis still has to take part during fermentation. In one embodiment, the fermentation time is 100 hours or less, 90 hours or less, 80 hours or less, 70 hours or less, or 60 hours or less, for a sugar composition of 50 g/l glucose and corresponding other sugars from the lignocellulosic material (e.g. 50 g/l xylose, 35 g/l L-arabinose and 10 g/l galactose). For more dilute sugar compositions, the fermentation time may correspondingly be reduced.

The fermentation process may be an aerobic or an anaerobic fermentation process. An anaerobic fermentation process is herein defined as a fermentation process run in the absence of oxygen or in which substantially no oxygen is consumed, preferably less than 5, 2.5 or 1 mmol/L/h, more preferably 0 mmol/L/h is consumed (i.e. oxygen consumption is not detectable), and wherein organic molecules serve as both electron donor and electron acceptors. In the absence of oxygen, NADH produced in glycolysis and biomass formation, cannot be oxidised by oxidative phosphorylation. To solve this problem many microorganisms use pyruvate or one of its derivatives as an electron and hydrogen acceptor thereby regenerating $NAD^+$. Thus, in a preferred anaerobic fermentation process pyruvate is used as an electron (and hydrogen acceptor) and is reduced to fermentation products such as ethanol, lactic acid, 3-hydroxy-propionic acid, acrylic acid, acetic acid, succinic acid, citric acid, malic acid, fumaric acid, an amino acid, 1,3-propane-diol, ethylene, glycerol, butanol, a $\beta$-lactam antibiotics and a cephalosporin. In a preferred embodiment, the fermentation process is anaerobic. An anaerobic process is advantageous, since it is cheaper than aerobic processes: less special equipment is needed. Furthermore, anaerobic processes are expected to give a higher product yield than aerobic processes. Under aerobic conditions, usually the biomass yield is higher than under anaerobic conditions. As a consequence, usually under aerobic conditions, the expected product yield is lower than under anaerobic conditions.

In another embodiment, the fermentation process is under oxygen-limited conditions. More preferably, the fermentation process is aerobic and under oxygen-limited conditions. An oxygen-limited fermentation process is a process in which the oxygen consumption is limited by the oxygen transfer from the gas to the liquid. The degree of oxygen limitation is determined by the amount and composition of the ingoing gas flow as well as the actual mixing/mass transfer properties of the fermentation equipment used. Preferably, in a process under oxygen-limited conditions, the rate of oxygen consumption is at least 5.5, more preferably at least 6 and even more preferably at least 7 mmol/L/h.

The fermentation process is preferably run at a temperature that is optimal for the modified cell. Thus, for most yeasts or fungal cells, the fermentation process is performed at a temperature which is less than 42° C., preferably less than 38° C. For yeast or filamentous fungal host cells, the fermentation process is preferably performed at a temperature which is lower than 35, 33, 30 or 28° C. and at a temperature which is higher than 20, 22, or 25° C.

In an embodiment of the invention, in step (h) the fermentation is conducted with a microorganism that is able to ferment at least one C5 sugar. In an embodiment the process is a process for the production of ethanol, wherein the process comprises the step of fermenting a medium containing sugar(s) with a microorganism that is able to ferment at least one C5 sugar. The microorganism may be a prokaryotic or eukaryotic organism. The microorganism used in the process may be a genetically engineered microorganism. Examples of suitable organisms are yeasts, for instance *Saccharomyces*, e.g. *Saccharomyces cerevisiae*, *Hansenula*, *Issatchenkia*, e.g. *Issatchenkia orientalis*, *Pichia*, e.g. *Pichia stipitis*, or bacteria, for instance *Lactobacillus*, e.g., *Lactobacillus lactis*, *Geobacillus*, *Zymomo-* nas, e.g. *Zymomonas mobilis, Clostridium*, e.g. *Clostridium phytofermentans*. In an embodiment the microorganism that is able to ferment at least one C5 sugar is a yeast. In an embodiment, the yeast is belongs to the genus *Saccharomyces*, preferably of the species *Saccharomyces cerevisiae*. The yeast, e.g. *Saccharomyces cerevisiae*, used in step (h) of the processes according to the present invention is capable of converting hexose (C6) sugars and pentose (C5) sugars. The yeast, e.g. *Saccharomyces cerevisiae*, used in step (h) of the processes according to the present invention can anaerobically ferment at least one C6 sugar and at least one C5 sugar. For example, the yeast is capable of using L-arabinose and xylose in addition to glucose anaerobically. In an embodiment, the yeast is capable of converting L-arabinose into L-ribulose and/or xylulose 5-phosphate and/or into a desired fermentation product, for example into ethanol. Organisms, for example *Saccharomyces cerevisiae* strains, able to produce ethanol from L-arabinose may be produced by modifying a host yeast introducing the araA (L-arabinose isomerase), araB (L-ribuloglyoxalate) and araD (L-ribulose-5-P4-epimerase) genes from a suitable source. Such genes may be introduced into a host cell in order that it is capable of using arabinose. Such an approach is given is described in WO2003/095627. araA, araB and araD genes from *Lactobacillus plantarum* may be used and are disclosed in WO2008/041840. The araA gene from *Bacillus subtilis* and the araB and araD genes from *Escherichia coli* may be used and are disclosed in EP1499708. In another embodiment, araA, araB and araD genes may derived from of at least one of the genus *Clavibacter, Arthrobacter* and/or *Gramella*, in particular one of *Clavibacter michiganensis, Arthrobacter aurescens*, and/or *Gramella forsetii*, as disclosed in WO 2009011591. In an embodiment, the yeast may also comprise one or more copies of xylose isomerase gene and/or one or more copies of xylose reductase and/or xylitol dehydrogenase.

The yeast may comprise one or more genetic modifications to allow the yeast to ferment xylose. Examples of genetic modifications are introduction of one or more xylA-gene, XYL1 gene and XYL2 gene and/or XKS1-gene; deletion of the aldose reductase (GRE3) gene; overexpression of PPP-genes TAL1, TKL1, RPE1 and RKI1 to allow the increase of the flux through the pentose phosphate pathway in the cell. Examples of genetically engineered yeast are described in EP1468093 and/or WO2006/009434.

An example of a suitable commercial yeast is RN1016 that is a xylose and glucose fermenting *Saccharomyces cerevisiae* strain from DSM, the Netherlands.

In an embodiment, the fermentation process for the production of ethanol is anaerobic. Anaerobic has already been defined earlier herein. In another preferred embodiment, the fermentation process for the production of ethanol is aerobic. In another preferred embodiment, the fermentation process for the production of ethanol is under oxygen-limited conditions, more preferably aerobic and under oxygen-limited conditions. Oxygen-limited conditions have already been defined earlier herein.

The volumetric ethanol productivity is preferably at least 0.5, 1.0, 1.5, 2.0, 2.5, 3.0, 5.0 or 10.0 g ethanol per litre per hour. The ethanol yield on L-arabinose and optionally xylose and/or glucose in the process preferably is at least 20, 25, 30, 35, 40, 45, 50, 60, 70, 80, 90, 95 or 98%. The ethanol yield is herein defined as a percentage of the theoretical maximum yield, which, for glucose and L-arabinose and optionally xylose is 0.51 g ethanol per g glucose or xylose.

In one aspect, the fermentation process leading to the production of ethanol, has several advantages by comparison to known ethanol fermentations processes: anaerobic processes are possible; oxygen limited conditions are possible; higher ethanol yields and ethanol production rates can be obtained; the strain used may be able to use L-arabinose and optionally xylose.

Alternatively to the fermentation processes described above, at least two distinct cells may be used, this means this process is a co-fermentation process. All preferred embodiments of the fermentation processes as described above are also preferred embodiments of this co-fermentation process: identity of the fermentation product, identity of source of L-arabinose and source of xylose, conditions of fermentation (aerobic or anaerobic conditions, oxygen-limited conditions, temperature at which the process is being carried out, productivity of ethanol, yield of ethanol).

The fermentation process may be carried out without any requirement to adjust the pH during the process. That is to say, the process is one which may be carried out without the addition of any acid(s) or base(s). However, this excludes a pretreatment step, where acid may be added. The point is that the enzyme composition used in the processes of the invention is capable of acting at low pH and, therefore, there is no need to adjust the pH of acid of an acid pretreated feedstock in order that hydrolysis may take place. Accordingly, the processes of the invention may be zero waste processes using only organic products with no requirement for inorganic chemical input.

The overall reaction time (or the reaction time of hydrolysis step and fermentation step together) may be reduced. In one embodiment, the overall reaction time is 300 hours or less, 200 hours or less, 150 hours or less, 140 hours or less, 130 or less, 120 hours or less, 110 hours or less, 100 hours of less, 90 hours or less, 80 hours or less, 75 hours or less, or about 72 hours at 90% glucose yield. Correspondingly, lower overall reaction times may be reached at lower glucose yield.

Fermentation products which may be produced by the processes of the invention include amino acids, vitamins, pharmaceuticals, animal feed supplements, specialty chemicals, chemical feedstocks, plastics, solvents, fuels, or other organic polymers, lactic acid, and ethanol, including fuel ethanol (the term "ethanol" being understood to include ethyl alcohol or mixtures of ethyl alcohol and water).

Specific value-added products that may be produced by the processes of the invention include, but not limited to, biofuels (including biogas, ethanol and butanol); lactic acid; 3-hydroxy-propionic acid; acrylic acid; acetic acid; 1,3-propane-diol; ethylene; glycerol; a plastic; a specialty chemical; an organic acid, including citric acid, succinic acid and maleic acid; a solvent; an animal feed supplement; a pharmaceutical such as a β-lactam antibiotic or a cephalosporin; a vitamin; an amino acid, such as lysine, methionine, tryptophan, threonine, and aspartic acid; an enzyme, such as a protease, a cellulase, an amylase, a glucanase, a lactase, a lipase, a lyase, an oxidoreductase, a transferase or a xylanase; a chemical feedstock; or an animal feed supplement.

The processes according to the invention optionally comprise recovery of fermentation product. A fermentation product may be separated from the fermentation broth in manner know to the skilled person. For each fermentation product the skilled person will thus be able to select a proper separation technique. For instance, ethanol may be separated from a yeast fermentation broth by distillation, for instance steam distillation/vacuum distillation in conventional way.

The beneficial effects of the present invention are found for several lignocellulosic materials and therefore believed to be present for the hydrolysis of all kind of lignocellulosic materials. This beneficial effects of the present invention are found for several enzyme compositions and therefore believed to be present for all kind of hydrolysing enzyme compositions.

EXAMPLES

Example 1

The Effect in Liquefaction of the Order of Addition of Lignocellulosic Material and Enzyme Composition to the Hydrolysis Container To show the effect of the order of addition of lignocellulosic material and enzyme composition to the hydrolysis container in the liquefaction process, the following experiments were conducted.

In two stirred containers A and B, a hydrolysis was performed with pretreated lignocellulosic material (cane straw 37% (w/w) dry matter) and an enzyme composition (100 mg eWB-CE enriched in BG/g DM) at a temperature of 62° C. and pH 4.5 for 8.4 hours.

TEC-210 cellulase-containing composition was produced as described in WO 2011/000949. The whole broth of the TEC-210 cellulase-containing composition (eWB-CE) comprised 44 mg protein/g whole broth.

Container A was filled with 349 g of 50 mM citric acid and then pretreated lignocellulosic material (called biomass in Table 1) was added. Next, the enzyme composition was added to the lignocellulosic material in the container. Thereafter, enzyme composition and lignocellulosic material were added to the container in a fed-batch mode as described in Table 1 (at t=0, 1.8 g of enzyme composition was added to 31 g of pretreated lignocellulosic material present in the container).

Container B was filled with 349 g of 50 mM citric acid and the total amount (24.2 g) of the enzyme composition and then pretreated lignocellulosic material was added in a fed-batch mode as described in Table 1 (at t=0, 31 g of pretreated lignocellulosic material was added to the total enzyme composition present in the container).

The viscosity of the hydrolysis mixture was followed during the hydrolysis and was determined with a Brookfield DV III Rheometer at 1 rpm and at a temperature of 62° C.

The final portions were added at 8.4 hours after the start of the enzymatic hydrolysis. At that point in time, container A and container B contained a total of 430 g of pretreated lignocellulosic material and 24.2 g of enzyme composition, which corresponds to 0.056 g of enzyme composition per g of pretreated lignocellulosic material. The dry matter content after 8.4 hours was 20% (w/w).

The results of the viscosity measurements are shown in Table 2. The results show that in container B, wherein lignocellulosic material is added to the container that already comprises enzyme composition, viscosity is lower than when enzyme composition is added to lignocellulosic material present into the container. In other words, when all enzymes are already present in the hydrolysis container at the start of the biomass feed-phase of the enzymatic hydrolysis, the viscosity is lower than when enzymes are added to the biomass. Lower viscosity reduces power input requirements for mixing, which are especially significant on large scale and facilitates reproducible sampling due to increased homogeneity of the liquefied lignocellulosic material during the feed phase. Having enzyme composition present in the container at the start of the enzymatic hydrolysis, like in container B, also simplifies processing, as only one stream has to be added to the container (in container B only lignocellulosic material has to be added, while in container A lignocellulosic material and enzyme composition needs to be added). This simplification reduces risks on process failures.

Example 2

The Effect in Liquefaction of Fed-Batch Addition and Batch Addition of Lignocellulosic Material to a Hydrolysis Container Comprising Enzyme Composition To demonstrate that fed-batch addition of lignocellulosic material (called biomass in Table 3) to a container containing enzyme composition has advantages over batch-wise addition of lignocellulosic material to a container containing enzyme composition, the following experiment was performed.

Eight similar containers containing the amounts of citric acid (50 mM, pH 4.5) and enzyme composition as given in Table 3 were heated to 62° C. Pretreated lignocellulosic material (cane straw of 37% (w/w) dry matter) was added batch-wise to containers 1 to 7 in the amounts given in Table 3, so that different dry matter contents were obtained at the start of the enzymatic hydrolysis.

Viscosity was measured using a Brookfield DV III Rheometer at a temperature of 62° C. after lignocellulosic material and enzyme composition were mixed. The viscosity measured is representative for the viscosity at the start of the enzymatic hydrolysis of lignocellulosic material at different contents of dry matter.

The lignocellulosic material was added in a fed-batch mode to container 8. The amount of citric acid buffer (2169 g) and enzyme composition (101 g) indicated in Table 3 were present at start of the enzymatic hydrolysis. Next, lignocellulosic material was added in portions (fed-batch) reaching the biomass levels given in Table 3. Time between each addition was 1 hour. Ergo, first 176 g of biomass was added to the container to a give a total amount of biomass of 176 g, after one hour 594 g of biomass was added to the container to give a total amount of biomass of 770 g, after another hour 392 g biomass was added to the container to give a total amount of biomass of 1162 g, etc. At the end of the fed batch addition of lignocellulosic material, 20% (w/w) dry matter with an enzyme dosage of 0.1 g enzyme per g biomass DM was obtained. Viscosity was measured using a Brookfield DV III Rheometer at a temperature of 62° C. after lignocellulosic material and enzyme composition were mixed.

Table 3 clearly demonstrates that fed-batch addition of lignocellulosic material to a container comprising enzyme composition leads to a lower viscosity than when lignocellulosic material is added batch-wise to a container comprising enzyme composition. This is the case for dry-matter contents above and below 10% (w/w).

TABLE 1

Addition of lignocellulosic material and enzyme composition during liquefaction in containers A and B.

| | Container A | | | Container B | | |
|---|---|---|---|---|---|---|
| Time (h) | Biomass (g) | Enzyme (g) | Enzyme/biomass (g/g) | Biomass (g) | Enzyme (g) | Enzyme/biomass (g/g) |
| 0 | 31 | 1.8 | 0.056 | 31 | 24.2 | 0.779 |
| 1.0 | 57 | 3.2 | 0.056 | 57 | | 0.275 |

TABLE 1-continued

Addition of lignocellulosic material and enzyme composition during liquefaction in containers A and B.

| | Container A | | | Container B | | |
|---|---|---|---|---|---|---|
| Time (h) | Biomass (g) | Enzyme (g) | Enzyme/ biomass (g/g) | Biomass (g) | Enzyme (g) | Enzyme/ biomass (g/g) |
| 2.1 | 57 | 3.2 | 0.056 | 57 | | 0.167 |
| 3.0 | 57 | 3.2 | 0.056 | 57 | | 0.120 |
| 4.3 | 57 | 3.2 | 0.056 | 57 | | 0.093 |
| 5.6 | 57 | 3.2 | 0.056 | 57 | | 0.077 |
| 7.4 | 57 | 3.2 | 0.056 | 57 | | 0.065 |
| 8.4 | 57 | 3.2 | 0.056 | 57 | | 0.056 |
| Total added (g) | 430 | 24.2 | | 430 | 24.2 | |

TABLE 2

Viscosity measurement.

| | Container A | Container B |
|---|---|---|
| Time (h) | Viscosity (cP) | |
| 0 | 0 | 0 |
| 1.0 | 0 | 0 |
| 2.1 | 0 | 0 |
| 3.0 | 2000 | 2000 |
| 4.3 | 8000 | 3000 |
| 5.6 | 24000 | 13000 |
| 7.4 | 39000 | 26000 |
| 8.4 | 74000 | 59000 |

TABLE 3

Content of containers 1 to 8 in which enzymatic hydrolysis was performed at different dry matter levels.

| Container | Citric acid (g) | Enzyme (g) | Biomass (g) | Enzyme/ Biomass DM (g/g) | Dry-matter content (% (w/w)) | Viscosity (cP) |
|---|---|---|---|---|---|---|
| 1 | 4341 | 23.5 | 635 | 0.10 | 4.7 | 98 |
| 2 | 4075 | 33.0 | 892 | 0.10 | 6.6 | 200 |
| 3 | 3809 | 42.5 | 1149 | 0.10 | 8.5 | 323 |
| 4 | 3669 | 47.5 | 1283 | 0.10 | 9.5 | 716 |
| 5 | 3542 | 52.0 | 1405 | 0.10 | 10.4 | 2345 |
| 6 | 3402 | 57.0 | 1541 | 0.10 | 11.4 | 5600 |
| 7 | 3276 | 61.5 | 1662 | 0.10 | 12.3 | 9829 |
| 8 | 2169 | 101 | 176 | 1.55 | 2.7 | 69 |
| | | | 770 | 0.35 | 9.4 | 61 |
| | | | 1162 | 0.23 | 12.5 | 194 |
| | | | 1473 | 0.19 | 14.6 | 813 |
| | | | 1746 | 0.16 | 16.1 | 1586 |
| | | | 1989 | 0.13 | 17.3 | 2257 |
| | | | 2205 | 0.12 | 18.2 | 2478 |
| | | | 2395 | 0.11 | 19.0 | 3142 |
| | | | 2565 | 0.11 | 19.6 | 3202 |
| | | | 2732 | 0.10 | 20.2 | 4108 |

What is claimed is:

1. A process for preparation of a sugar product from lignocellulosic material, comprising:
   a) optionally, pretreatment of the lignocellulosic material;
   b) optionally, washing of the optionally pretreated lignocellulosic material;
   c) fed-batch addition of the optionally washed and/or optionally pretreated lignocellulosic material to a first container that comprises an enzyme composition comprising at least two cellulases;
   d) enzymatic hydrolysis of the optionally washed and/or optionally pretreated lignocellulosic material in the first container using the enzyme composition comprising at least two cellulases to liquefy the lignocellulosic material;
   e) addition of the liquefied lignocellulosic material to a second container;
   f) enzymatic hydrolysis of the liquefied lignocellulosic material in the second container using an enzyme composition comprising at least two cellulases to obtain a sugar product; and
   g) optionally, recovery of the sugar product.

2. A process for preparation of a fermentation product from lignocellulosic material, comprising:
   a) optionally, pretreatment of the lignocellulosic material;
   b) optionally, washing of the optionally pretreated lignocellulosic material;
   c) fed-batch addition of the optionally washed and/or optionally pretreated lignocellulosic material to a first container that comprises an enzyme composition comprising at least two cellulases;
   d) enzymatic hydrolysis of the optionally washed and/or optionally pretreated lignocellulosic material in the first container using the enzyme composition comprising at least two cellulases to liquefy the lignocellulosic material;
   e) addition of the liquefied lignocellulosic material to a second container;
   f) enzymatic hydrolysis of the liquefied lignocellulosic material in the second container using an enzyme composition comprising at least two cellulases to obtain a hydrolysed lignocellulosic material;
   g) optionally, recovery of the hydrolysed lignocellulosic material;
   h) fermentation of the hydrolysed lignocellulosic material to produce a fermentation product; and
   i) optionally, recovery of the fermentation product.

3. The process according to claim 1, wherein additional enzymes are added during (d) and/or (f).

4. The process according to claim 1, wherein the viscosity of the lignocellulosic material in the first container during (d) is controlled by adjusting the addition rate of the optionally washed and/or optionally pretreated lignocellulosic material.

5. The process according to claim 4, wherein the viscosity of the lignocellulosic material in the first container during (d) is kept below 1000 cP.

6. The process according to claim 1, wherein an aqueous composition, optionally an aqueous enzyme composition comprising at least two cellulases, is added to the first container.

7. The process according to claim 1, wherein the first container and/or second container has a volume of at least 1 m$^3$.

8. The process according to claim 1, wherein the enzymatic hydrolysis time in (d) is 3 to 24 hours.

9. The process according to claim 1, wherein the enzymatic hydrolysis time in (f) is 3 to 120 hours.

10. The process according to claim 1, wherein the enzymatic hydrolysis in (d) and/or (f) is conducted at a temperature of 45° C. or more, optionally 50° C. or more and optionally at a temperature of 55° C. or more.

11. The process according to claim 1, wherein the enzyme composition is derived from a fungus, optionally a microorganism of the genus *Rasamsonia*, or the enzyme composition comprises a fungal enzyme, optionally a *Rasamsonia* enzyme.

12. The process according to claim 2, wherein the fermentation in (h) is performed in the second container.

13. The process according to claim 1, wherein the dry matter content at the end of the hydrolysis of (f) is 5 wt % or higher.

14. The process according to claim 1, wherein the enzyme composition is a whole fermentation broth.

15. The process according to claim 2, wherein the fermentation in (h) is conducted with a microorganism that is able to ferment at least one C5 sugar.

* * * * *